US 6,534,308 B1

(12) United States Patent
Palsson et al.

(10) Patent No.: US 6,534,308 B1
(45) Date of Patent: Mar. 18, 2003

(54) METHOD AND APPARATUS FOR SELECTIVELY TARGETING SPECIFIC CELLS WITHIN A MIXED CELL POPULATION

(75) Inventors: Bernhard O. Palsson, La Jolla, CA (US); Manfred R. Koller, San Diego, CA (US); Timothy M. Eisfeld, La Jolla, CA (US)

(73) Assignee: Oncosis, LLC, San Diego, CA (US)

( * ) Notice: Subject to any disclaimer, the term of this patent is extended or adjusted under 35 U.S.C. 154(b) by 0 days.

(21) Appl. No.: 09/451,659

(22) Filed: Nov. 30, 1999

Related U.S. Application Data

(63) Continuation-in-part of application No. 09/049,677, filed on Mar. 27, 1998, now Pat. No. 6,143,535, which is a continuation-in-part of application No. 08/824,968, filed on Mar. 27, 1997, now Pat. No. 5,874,266.

(51) Int. Cl.[7] .................. C12M 1/34; C12N 13/00
(52) U.S. Cl. .............. 435/288.7; 435/7.2; 435/34; 435/460; 435/173.5; 435/173.7; 435/287.2; 382/133
(58) Field of Search .................. 435/4, 29, 7.2, 435/173.1, 34, 285.1, 288.7, 287.2, 173.4, 173.5, 173.7, 460; 382/129, 133, 134

(56) References Cited

U.S. PATENT DOCUMENTS

| 3,674,926 | A | * | 7/1972 | Dewey et al. |
| 4,284,897 | A | | 8/1981 | Sawamura et al. |
| 4,395,397 | A | | 7/1983 | Shapiro |
| 4,532,402 | A | | 7/1985 | Overbeck |
| 4,624,915 | A | | 11/1986 | Schindler et al. |
| 4,629,687 | A | | 12/1986 | Schindler et al. |
| 4,803,992 | A | | 2/1989 | Lemelson |
| 5,013,660 | A | * | 5/1991 | Kasuya et al. |
| 5,035,693 | A | | 7/1991 | Kratzer et al. |
| 5,089,384 | A | | 2/1992 | Hale |
| 5,158,889 | A | | 10/1992 | Hirako et al. |
| 5,188,633 | A | | 2/1993 | Kratzer et al. |
| 5,272,081 | A | | 12/1993 | Weinreb et al. |
| 5,296,963 | A | | 3/1994 | Murakami et al. |
| 5,381,224 | A | | 1/1995 | Dixon et al. |
| 5,523,543 | A | * | 6/1996 | Hunter, Jr. et al. |
| 5,646,411 | A | | 7/1997 | Kain et al. |
| 5,672,880 | A | | 9/1997 | Kain |
| 5,690,846 | A | | 11/1997 | Okada et al. |
| 5,719,391 | A | | 2/1998 | Kain |
| 5,785,703 | A | * | 7/1998 | Goodman et al. |
| 5,795,755 | A | * | 8/1998 | Lemelson |
| 5,874,266 | A | | 2/1999 | Palsson |
| 5,932,872 | A | | 8/1999 | Price |
| 6,005,256 | A | * | 12/1999 | McGlynn et al. |
| 6,040,139 | A | * | 3/2000 | Bova .................. 435/284.1 |
| 6,122,396 | A | * | 9/2000 | King et al. |
| 6,148,096 | A | * | 11/2000 | Pressman et al. |

FOREIGN PATENT DOCUMENTS

| JP | 63-259465 A | * 10/1988 |
| WO | WO 98/52016 | 11/1998 |

OTHER PUBLICATIONS

International Search Report from PCT/US00/32742, Mar. 23, 2001.

(List continued on next page.)

Primary Examiner—William H. Beisner
(74) Attorney, Agent, or Firm—Knobbe Martens Olson & Bear, LLP

(57) ABSTRACT

This invention provides a method and apparatus for selectively identifying, and targeting with an energy beam, specific cells within a mixed cell population, for the purpose of inducing a response in the targeted cells. Using the present invention, every detectable cell in a population can be identified and affected, without substantially affecting non-targeted cells within the mixture.

94 Claims, 7 Drawing Sheets

OTHER PUBLICATIONS

Photonic Instruments, Inc.; *Micro Point–Laser System For Bio–Medical and Life Sciences*; Product Information Sheet, Apr. 1996.

Gribben, et al.; Antibody–mediated Purging; *Bone Marrow Transplantation*; Chapter 13, Boston–Blackwell Scientific Publications; pp. 149–163 (1994).

Rowley, Scott D.; Pharmacological Purging of Malignant Cells; *Bone Marrow Transplantation*; Chapter 14, Boston-Blackwell Scientific Publications; pp. 164–178 (1994).

Gee, Adrian P.; Part 5: Autologous Bone Marrow Purging; *Bone Marrow Processing and Purging*; pp. 248–328 (1991).

Dooley, et al.; A Novel, *Inexpensive Technique for the Removal of Breast Cancer Cells from Mobilized Peripheral Blood Stem Cell Products*; Blood; vol. 88; p. 252a (1996).

Greer, et al.; *A Clonogenic Culture Method for the Identification of Breast Cancer Cells in Marrow Aspirates of Patients Receiving High–Dose Chemotherapy*; Abstract 996, 439–II; *Blood* (1996).

Thomas, et al.; *Direct Purging of Breast Carcinoma Cells with Anti–CD24 and/or Anti–Breast Carcinoma Antibodies Using a Novel Immunomagnetic Cell Depletion System*; Blood (1996).

Theocharous, et al.; *The Detection and Genetic Analysis of Low Frequency Epithlial Tumour Cells in Patients with Breast Cancer*; Blood (1996).

Miller, et al.; *Rapid Killing of Single Neurons by Irradiation of Intracellularly Injected Dye; Science*; vol. 206; Nov. 9, 1979; pp. 702–704.

Lazarus, et al.; Does In Vitro *Bone Marrow Purging Improve the Outcome after Autologous Bone Marrow Transplantation?*; Journal of Hematotherapy; 1993; 2:457–466.

Gulati, et al.; *Rationale for Purging in Autologous Stem Cell Transplantation*; Journal of Hematotherapy; 1993; 2:467–471.

Brugger, et al.; *Mobilization of Tumor Cells and Hematopoietic Progenitor Cells Into Peripheral Blood of Patients with Solid Tumors*; Blood; vol. 83; No. 3; Feb. 1, 1994; pp. 636–640.

Rill, et al.; *Direct Demonstration that Autologous Bone Marrow Transplantation for Solid Tumors Can Return a Multiplicity of Tumorigenic Cells*; Blood; vol. 84, No. 2; Jul. 15, 1994; pp. 380–383.

Campana, et al.; *Detection of Minimal Residual Disease in Acute Leukemia: Methodologic Advances and Clinical Significance*; Blood; vol. 85; No. 6; Mar. 15, 1995; pp. 1416–1434.

Gazitt, et al.; *Purified CD34+Lin–Thy+Stem Cells Do Not Contain Clonal Myeloma Cells*; Blood; vol. 86; No. 1; Jul. 1, 1995; pp. 381–389.

Clarke, et al.; *A recombinant bcl–xs adenovirus selectively induces apoptosis in cancer cells but not in normal bone marrow cells*; Proc. Natl. Acad. Sci. USA; vol. 92; Nov. 1995; pp. 11024–11028.

Lydaki, et al.; *Merocyanine 540 mediated photoirradiation of leukemic cells. In vitro inference on cell survival*; Journal of Photochemistry and Photobiology B: Biology 32; pp. 27–32.

* cited by examiner

METHOD AND APPARATUS FOR SELECTIVELY TARGETING SPECIFIC CELLS WITHIN A MIXED CELL POPULATION

RELATED APPLICATION

This application is a continuation-in-part of U.S. patent application Ser. No. 09/049,677, filed on Mar. 27, 1998 now U.S. Pat. No. 6,143,535 which is a continuation-in-part of U.S. patent application Ser. No. 08/824,968, filed on Mar. 27, 1997, now U.S. Pat. No. 5,874,266, issued on Feb. 23, 1999.

BACKGROUND OF THE INVENTION

1. Field of the Invention

This invention relates to methods and apparatus for selectively targeting specific cells within a mixed population of living cells. In particular, this invention relates to high-speed methods and apparatus for selectively identifying, and individually targeting with an energy beam, specific cells within a mixed cell population to induce a response in the targeted cells.

2. Description of the Related Art

The use of cellular therapies is growing rapidly, and is therefore becoming an important therapeutic modality in the practice of medicine. Unlike other therapies, cellular therapies achieve a long-lasting, and often permanent benefit through the use of living cells. Hematopoietic stem cell (HSC) (e.g., bone marrow or mobilized peripheral blood) transplantation is one example of a practiced, insurance-reimbursed cellular therapy. Many other cellular therapies are being developed, including immunotherapy for cancer and infectious diseases, chondrocyte therapy for cartilage defects, neuronal cell therapy for neurodegenerative diseases, and stem cell therapy for numerous indications. Many of these therapies require the removal of unwanted, detrimental cells for full efficacy to be realized.

Gene therapy is another active area of developing medicine that can influence the success of cellular therapy. Given the rapid advances in the understanding of the human genome, it is likely that many genes will be available for insertion into cells prior to transplantation into patients. However, obtaining efficient targeted delivery of genes into specific cells of interest has remained a difficult obstacle in the development of these therapies.

In the treatment of cancer, it has been found that high-dose chemotherapy and/or radiation therapy can be used to selectively kill rapidly dividing cancer cells in the body. Unfortunately, several other cell types in the body are also rapidly dividing, and in fact, the dose-limiting toxicity for most anti-cancer therapies is the killing of HSCs and progenitor cells in the bone marrow. HSC transplantation was developed as a therapy to rescue the hematopoietic system following anti-cancer treatments. Upon infusion, the HSCs and progenitor cells within the transplant selectively home to the bone marrow and engraft. This process is monitored clinically through daily blood cell counts. Once blood counts return to acceptable levels, usually within 20 to 30 days, the patient is considered engrafted and is released from the hospital.

HSC transplants have been traditionally performed with bone marrow, but mobilized peripheral blood (obtained via leukapheresis after growth factor or low-dose chemotherapy administration) has recently become the preferred source because it eliminates the need to harvest approximately one liter of bone marrow from the patient. In addition, HSCs from mobilized peripheral blood result in more rapid engraftment (8 to 15 days), leading to less critical patient care and earlier discharge from the hospital. HSC transplantation has become an established therapy for treating many diseases, such that over 45,000 procedures were performed worldwide in 1997.

HSC transplantation may be performed using either donor cells (allogeneic), or patient cells that have been harvested and cryopreserved prior to administration of high-dose anti-cancer therapy (autologous). Autologous transplants are widely used for treating a variety of diseases including breast cancer, Hodgkin's and non-Hodgkin's lymphomas, neuroblastoma, and multiple myeloma. The number of autologous transplants currently outnumbers allogeneic transplants by approximately a 2:1 ratio. This ratio is increasing further, mainly due to graft-versus-host disease (GVHD) complications associated with allogeneic transplants. One of the most significant problems with autologous transplants is the reintroduction of tumor cells to the patient along with the HSCs, because these tumor cells contribute to relapse of the original disease.

As a tumor grows, tumor cells eventually leave the original tumor site and migrate through the bloodstream to other locations in the body. This process, called tumor metastasis, results in the formation and growth of satellite tumors that greatly increase the severity of the disease. The presence of these metastatic tumor cells in the blood and other tissues, often including bone marrow, can create a significant problem for autologous transplantation. In fact, there is a very high probability that metastatic tumor cells will contaminate the harvested HSCs that are to be returned to the patient following anti-cancer therapy.

The presence of contaminating tumor cells in autologous bone marrow and mobilized peripheral blood harvests has been confirmed in numerous scientific studies. Tumor cell contamination has been repeatedly observed in patients with T-cell lymphoma, non-Hodgkin's lymphoma, leukemia, neuroblastoma, lung cancer, breast cancer, etc. (Brugger et al. 1994; Gulati and Acaba 1993; Kvalheim et al. 1996; Mapara et al. 1997; Paulus et al. 1997; Shpall and Jones 1994; Vervoordeldonk et al. 1997). In every study, all or nearly all of the patient samples analyzed were positive for tumor contamination. The level of tumor cell burden in these HSC harvests varied widely depending upon the type and stage of disease. Typical numbers indicate that tumor cells are present in the range of 3 to 3,000 tumor cells per million hematopoietic cells. Since the transplanted cell number is on the order of 10 billion hematopoietic cells, the total number of tumor cells in a transplant varies in the range of 30 thousand to 30 million. The reinfusion of this number of tumor cells in the HSC transplant following the patient's anti-cancer therapy is of considerable clinical concern. In fact, animal models have shown that as few as 25 leukemia cells can establish a lethal tumor in 50% of mice, and these numbers extrapolate to 3500 cells in humans (Gulati, Acaba 1993).

Recent landmark studies have unambiguously shown that reinfused tumor cells do indeed contribute to disease relapse in humans (Rill et al. 1994). This was proven by genetically marking the harvested cells prior to transplant, and then showing that the marker was detected in resurgent tumor cells in those patients who relapsed with disease. These data have been confirmed by other investigators (Deisseroth et al. 1994), indicating that contaminating tumor cells in HSC transplants represent a real threat to patients undergoing autologous transplantation.

Subsequent detailed studies have now shown that the actual number of tumor cells reinfused in the transplant was correlated with the risk of relapse for acute lymphoblastic leukemia (Vervoordeldonk et al. 1997), non-Hodgkin's lymphoma (Sharp et al. 1992; Sharp et al. 1996), mantle cell lymphoma (Andersen et al. 1997), and breast cancer (Brockstein et al. 1996; Fields et al. 1996; Schulze et al. 1997; Vannucchi et al. 1998; Vredenburgh et al. 1997). One of these studies went even further, showing that the number of tumor cells infused was inversely correlated with the elapsed time to relapse (Vredenburgh et al. 1997). These data suggest that reducing the number of tumor cells in the transplant will lead to better outcomes for the patient.

In fact, one clinical study of NHL purging in 114 patients showed that disease-free survival (after a median 2-year follow-up) was substantially higher (93%) in the subset of patients that had all detectable tumor cells purged prior to transplant, as compared with those in which purging was unsuccessful (54%) (Gribben et al. 1991). In a recent update of this study, eight-year freedom-from-relapse was shown to be 83% in the subset of patients that had all detectable tumor cells purged, as compared to 19% in patients where purging was unsuccessful (Freedman et al. 1999). Therefore, the actual number of tumor cells in an HSC transplant, and the ability to reliably purge them, are of significant and growing importance in the delivery of HSC transplantation therapies for cancer patients.

Due to the known risk of tumor cell contamination in autologous transplantation, a number of methods have been proposed for removing contaminating tumor cells from harvested HSC populations. The basic principle underlying all purging methods is to remove or kill tumor cells while preserving the HSCs that are needed for hematopoietic reconstitution in the patient.

One method based on relatively non-specific adhesion differences of hematopoietic cells in deep bed filtration has been described by Dooley, et al. (Dooley et al. 1996). An elutriation method based on relatively non-specific cell size and density differences has been described by Wagner, et al. (Wagner et al. 1995). Preferential killing of tumor cells by hyperthermia has been described by Higuchi, et al. (Higuchi et al. 1991). These relatively non-specific methods reduce the number of tumor cells present, but a significant number are known to remain.

In another method, cytotoxic agents, such as 4-hydroxy-peroxy-cyclophosphamide (4-HC), were used to preferentially kill tumor cells in populations containing HSCs (Bird et al. 1996). Unfortunately, collateral damage to normal HSCs was so severe that patient engraftment was delayed by as much as 59 days.

Another method employed preferential killing of tumor cells by exposing all cells to photoradiation in the presence of a light-sensitizing agent (e.g. merocyanide) (Gulliya and Pervaiz 1989). Although more tumor cells were killed than hematopoietic cells, some tumor cells still remained, and HSC damage was significant.

Another method for removing tumor cells from populations of hematopoietic cells involved immunoconjugating a toxic agent to an antibody having specificity for the tumor cells. In this system, antibodies were bound to chemotoxic agents, toxins, or radionucleides and then contacted with the total cell population. Unfortunately, not all of the tumor cells were killed by this treatment (Gribben et al. 1991; Robertson et al. 1992).

Some companies and physicians have attempted to purge malignant cells from populations of non-tumor cells using an immunoaffinity bead-based selection. In this procedure, the total cell population is contacted by immunoaffinity beads. For example, a first (positive) CD34-selection procedure enriches HSCs from the tumor cell-containing hematopoietic cell mixture. In some instances, a second (negative) immunoaffinity bead-based selection is also performed using anti-tumor or anti-epithelial cell antibodies attached to the beads. Although these procedures enrich HSCs and reduce tumor cell numbers, tumor cells can still be detected in the final product (Mapara et al. 1999) In another protocol, Clarke et al. disclosed the use of adenovirus-mediated transfer of suicide genes to selectively kill tumor cells (Clarke et al. 1995). However, it is well known that virus-mediated gene transfer is far less than 100% efficient, which would result in a significant number of tumor cells being unaffected by the protocol.

Yet another method utilized fluorescence-activated cell sorting (FACS) to sort HSCs from tumor cells (Tricot et al. 1995). As is known, flow cytometry sorts cells one at a time and physically separates one population of cells from a mixture of cells based upon cell surface markers and physical characteristics. However, it has been shown that using FACS to separate large cell populations for clinical applications is not advantageous because the process is slow, the cell yields can be very low, and purity greater than ~98% is rarely achieved.

Another method utilizing a flow cytometer is described in U.S. Pat. No. 4,395,397 to Shapiro. In the Shapiro method, labeled cells are placed in a flow cytometer, and a downstream laser beam is used to kill the labeled cells in the flowing stream after they pass by the detector and are recognized as being labeled by the electronic system. This method suffers from a number of disadvantages. Firstly, once an unwanted cell has passed through the detector/laser region there is no way to check that destruction has been completed successfully. If a tumor cell evades destruction it will inevitably be reintroduced into the patient. Secondly, the focal spot diameter of the laser beam is of necessity greater than the liquid stream cross section. Accordingly, many of the HSCs in the region of an unwanted cell will also be destroyed by the laser beam. Also, as described above, the purity obtained by flow cytometric techniques is not very good due to the random and dynamic nature of a heterogeneous cell mixture that is flowing in a fast-moving (1–20 m/sec) stream of liquid.

Another method that utilizes laser technology is described in U.S. Pat. No. 4,629,687 to Schindler, et al. In this method, anchorage-dependent cells are grown on a movable surface, and then a small laser beam spot is scanned across the moving surface to illuminate cells one at a time and the information is recorded. The same laser is then switched to a higher lethal power level, and the beam is swept over the surface in all areas except where a cell of interest was recorded during the illumination step. Unfortunately, this method is slow and only will work on cells that can adhere to a surface.

A still further method that utilizes laser technology is described in U.S. Pat. No. 5,035,693 to Kratzer. In this method, cells are placed on a moving belt and a small laser beam spot is scanned across the surface. When a particular cell radiates in response to the illuminating laser spot, the same laser is quickly switched to high power in order to kill the cell in a near simultaneous manner before the scanner has moved appreciably away from that cell. However, this system has many of the same disadvantages as the Shapiro method. For example, because the scanner is continuously moving during the imaging and killing of cells, the system is highly-dynamic, and therefore less stable and less accurate than a static system. Also, because the cells are moving on a belt past the detector in one direction, the method is not reversible. Thus, if a single tumor cell escapes detection, it will be reintroduced into the patient.

Others have used a small laser beam spot to dynamically scan over a surface to illuminate cells. For example, U.S. Pat. No. 4,284,897 to Sawamura et al. describes the use of galvanometric mirrors to scan a small laser beam spot in a standard microscope to illuminate fluorescent cells. U.S. Pat. No. 5,381,224 to Dixon et al. describes imaging of macroscopic specimens through the use of a laser beam spot that is raster-scanned with galvanometric mirrors through an F-theta scanning lens. In U.S. Pat. Nos. 5,646,411, 5,672,880, and 5,719,391 to Kain, scanning of a small laser spot with galvanometers through an F-theta lens is described. All of these imaging methods dynamically illuminate a small point that is moved over the surface to be imaged. In some cases, the surface being scanned is also moving during imaging.

Similar methods of scanning a small laser spot have been described for purposes other than imaging of cells. For example, U.S. Pat. No. 4,532,402 to Overbeck describes the use of galvanometers to move a small laser beam spot over a semiconductor surface for repair of an integrated circuit. Similarly, U.S. Pat. No. 5,690,846 to Okada et al. describes laser processing by moving a small laser spot with mirrors through an F-theta scanning lens. U.S. Pat. No. 5,296,963 to Murakami et al. describes the use of galvanometric mirrors to scan a small laser beam spot in a standard inverted microscope to puncture cells for insertion of genetic matter.

Yet another method of scanning a biological specimen is described in U.S. Pat. No. 5,932,872 to Price. This method uses a plurality of detectors to simultaneously capture images at a plurality of focus planes from a constantly moving surface. The resultant images can be used to choose the best-focus image in real-time, and can be used to generate a three-dimensional volumetric image of a specimen.

Most of the methods described above are based on administering a tumor cell-removal or tumor cell-killing strategy to the entire harvested cell population as a whole. In flow cytometry, cells are sorted on a single cell basis to physically separate the unwanted tumor cells from HSCs. While each of these methods has been shown to reduce tumor cell numbers in HSC transplants, none has demonstrated the ability to remove or kill all detectable tumor cells. In fact, the majority of patient transplants still contain detectable tumor cells after these purging techniques are used. Approximately 30 to 30,000 tumor cells per transplant still remain, even after multiple-step purging procedures (Gazitt et al. 1995; Gribben et al. 1991; Mapara et al. 1997; Paulus et al. 1997). Further, all of these methods result in some degree of HSC loss or damage, which can significantly impact the success of the HSC transplant by delaying patient engraftment. In summary, existing purging technologies are inadequate, and there exists a great unmet clinical need for novel approaches that can effectively purge all detectable tumor cells from an HSC transplant. The method and apparatus described herein fulfills this need.

SUMMARY OF THE INVENTION

This invention provides a high-speed method and apparatus for selectively identifying, and individually targeting with an energy beam, specific cells within a mixed cell population of cells for the purpose of inducing a response in the targeted cells. Using the apparatus of the present invention, every detectable target cell in a mixed cell population can be specifically identified and targeted, without substantially affecting cells that are not being targeted.

Specific cells are identified with the disclosed invention using several approaches. One embodiment includes a non-destructive labeling method so that all of the cells of a first population are substantially distinguishable from the remaining cells of the cell mixture, the remaining cells comprising the second population. In this embodiment, a labeled antibody can be used to specifically mark each cell of the first population, yet not mark cells of the second population. The labeled cells are then identified within the cell mixture. A narrow energy beam is thereafter focused on the first of the targeted cells to achieve a desired response. The next of the targeted cells is then irradiated, and so on until every targeted cell has been irradiated.

In another embodiment, an antibody that selectively binds to cells of the second population, but not cells of the first population, is used to identify cells of the first population. Cells of the first population are identified by the absence of the label, and are thereafter individually targeted with the energy beam.

The nature of the response that is induced by the energy beam is dependent upon the nature of the energy beam. Responses that can be induced with an energy beam include necrosis, apoptosis, optoporation (to allow entry of a substance that is present in the surrounding medium, including genetic material), cell lysis, cell motion (laser tweezers), cutting of cell components (laser scissors), activation of a photosensitive substance, excitation of a fluorescent reagent, etc.

A large number of commercially important research and clinical applications can be envisioned for such an apparatus, examples of which are presented below.

DETAILED DESCRIPTION

Figure 1:
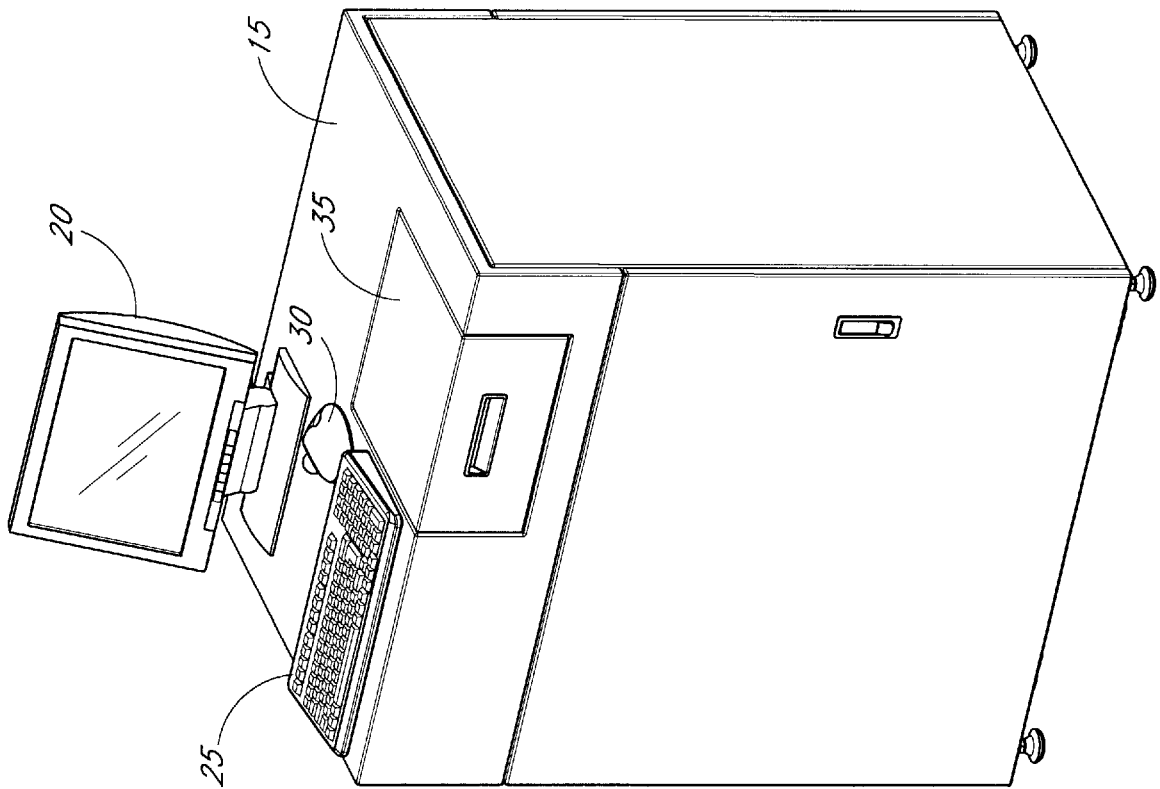
FIG. 1 is a perspective view of one embodiment of a cell treatment apparatus and illustrates the outer design of the housing and display.

A method and apparatus is described for selectively identifying, and individually targeting with an energy beam, specific cells within a mixed cell population for the purpose of inducing a response in the targeted cells. Generally, the method first employs a label that acts as a marker to identify and locate individual cells of a first population of cells within a cell mixture that is comprised of the first population of cells and a second population of cells.

The chosen label can be any that substantially identifies and distinguishes the first population of cells from the second population of cells. For example, monoclonal antibodies that are directly or indirectly tagged with a fluorochrome can be used as specific labels. Other examples of cell surface binding labels include non-antibody proteins, lectins, carbohydrates, or short peptides with selective cell binding capacity. Membrane intercalating dyes, such as PKH-2 and PKH-26, could also serve as a useful distinguishing label indicating mitotic history of a cell. Many membrane-permeable reagents are also available to distinguish living cells from one another based upon selected criteria. For example, phalloidin indicates membrane integrity, tetramethyl rhodamine methyl ester (TMRM) indicates mitochondrial transmembrane potential, monochlorobimane indicates glutathione reductive stage, carboxymethyl fluorescein diacetate (CMFDA) indicates thiol activity, carboxyfluorescein diacetate indicates intracellular pH, fura-2 indicates intracellular $Ca^{2+}$level, and 5,5',6,6'-tetrachloro-1,1',3,3'-tetraethylbenzimidazolo carbocyanine iodide (JC-1) indicates membrane potential. Cell viability can be assessed by the use of fluorescent SYTO 13 or YO PRO reagents. Similarly, a fluorescently-tagged genetic probe (DNA or RNA) could be used to label cells which carry a gene of interest, or express a gene of interest. Further, cell cycle status could be assessed through the use of Hoechst 33342 dye to label existing DNA combined with bromodeoxyuridine (BrdU) to label newly synthesized DNA.

It should be noted that if no specific label is available for cells of the first population, the method can be implemented in an inverse fashion by utilizing a specific label for cells of the second population. For example, in hematopoietic cell populations, the CD34 or ACC-133 cell markers can be used to label only the primitive hematopoietic cells, but not the other cells within the mixture. In this embodiment, cells of the first population are identified by the absence of the label, and are thereby targeted by the energy beam.

After cells of the first population are identified, an energy beam, such as from a laser, collimated or focused non-laser light, RF energy, accelerated particle, focused ultrasonic energy, electron beam, or other radiation beam, is used to deliver a targeted dose of energy that induces the predetermined response in each of the cells of the first population, without substantially affecting cells of the second population.

FIG. 1 is an illustration of one embodiment of a cell treatment apparatus 10. The cell treatment apparatus 10 includes a housing 15 that stores the inner components of the apparatus. The housing includes laser safety interlocks to ensure safety of the user, and also limits interference by external influences (e.g., ambient light, dust, etc.). Located on the upper portion of the housing 15 is a display unit 20 for displaying captured images of cell populations during treatment. These images are captured by a camera, as will be discussed more specifically below. A keyboard 25 and mouse 30 are used to input data and control the apparatus 10. An access door 35 provides access to a movable stage that holds a specimen container of cells undergoing treatment.

Figure 2:
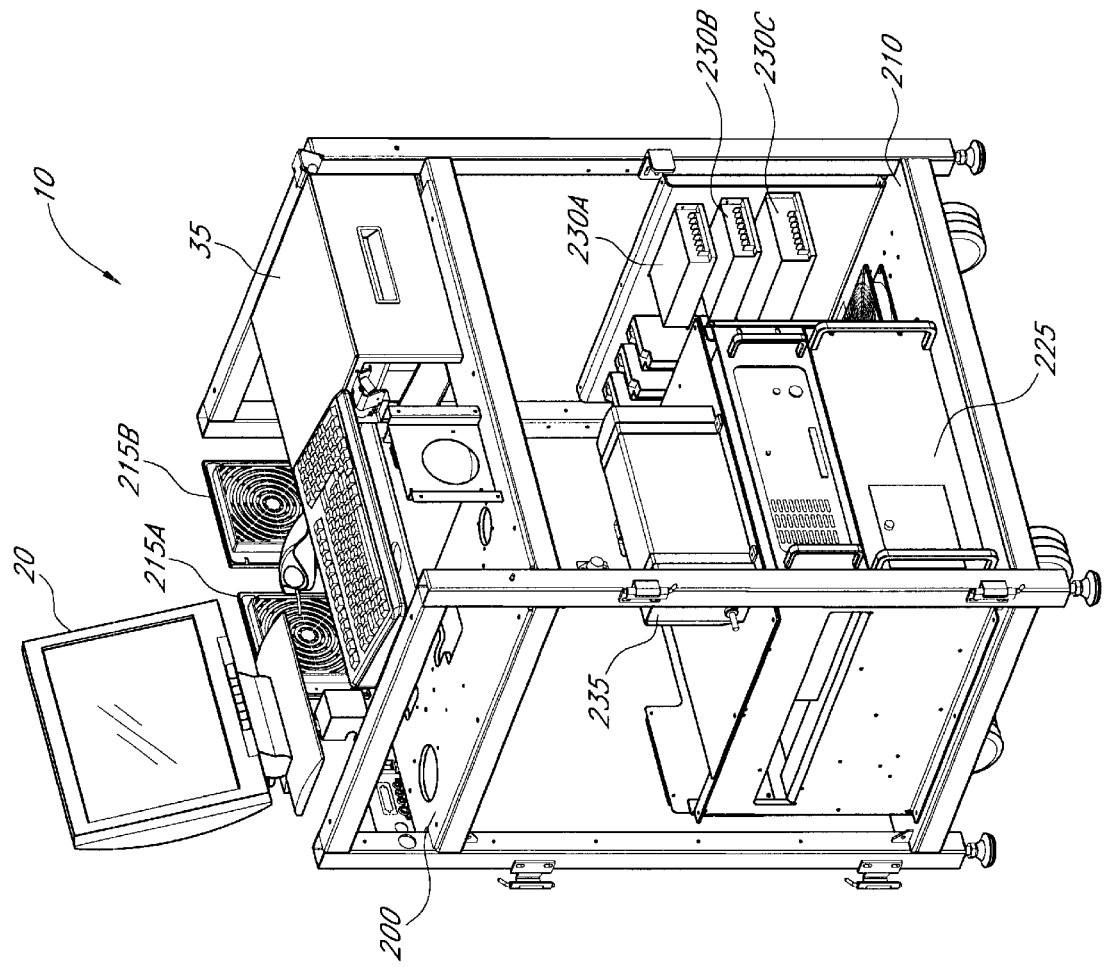
FIG. 2 is a perspective view of one embodiment of a cell treatment apparatus with the outer housing removed and the inner components illustrated.

An interior view of the apparatus 10 is provided in FIG. 2. As illustrated, the apparatus 10 provides an upper tray 200 and lower tray 210 that hold the interior components of the apparatus. The upper tray 200 includes a pair of intake filters 215A,B that filter ambient air being drawn into the interior of the apparatus 10. Below the access door 35 is the optical subassembly (not shown). The optical subassembly is mounted to the upper tray 200 and is discussed in detail with regard to FIGS. 3–6.

On the lower tray 210 is a computer 225 which stores the software programs, commands and instructions that run the apparatus 10. In addition, the computer 225 provides control signals to the treatment apparatus through electrical signal connections for steering the laser to the appropriate spot on the specimen in order to treat the cells.

As illustrated, a series of power supplies 230A,B,C provide power to the various electrical components within the apparatus 10. In addition, an uninterruptable power supply 235 is incorporated to allow the apparatus to continue functioning through short external power interruptions.

Figure 3:
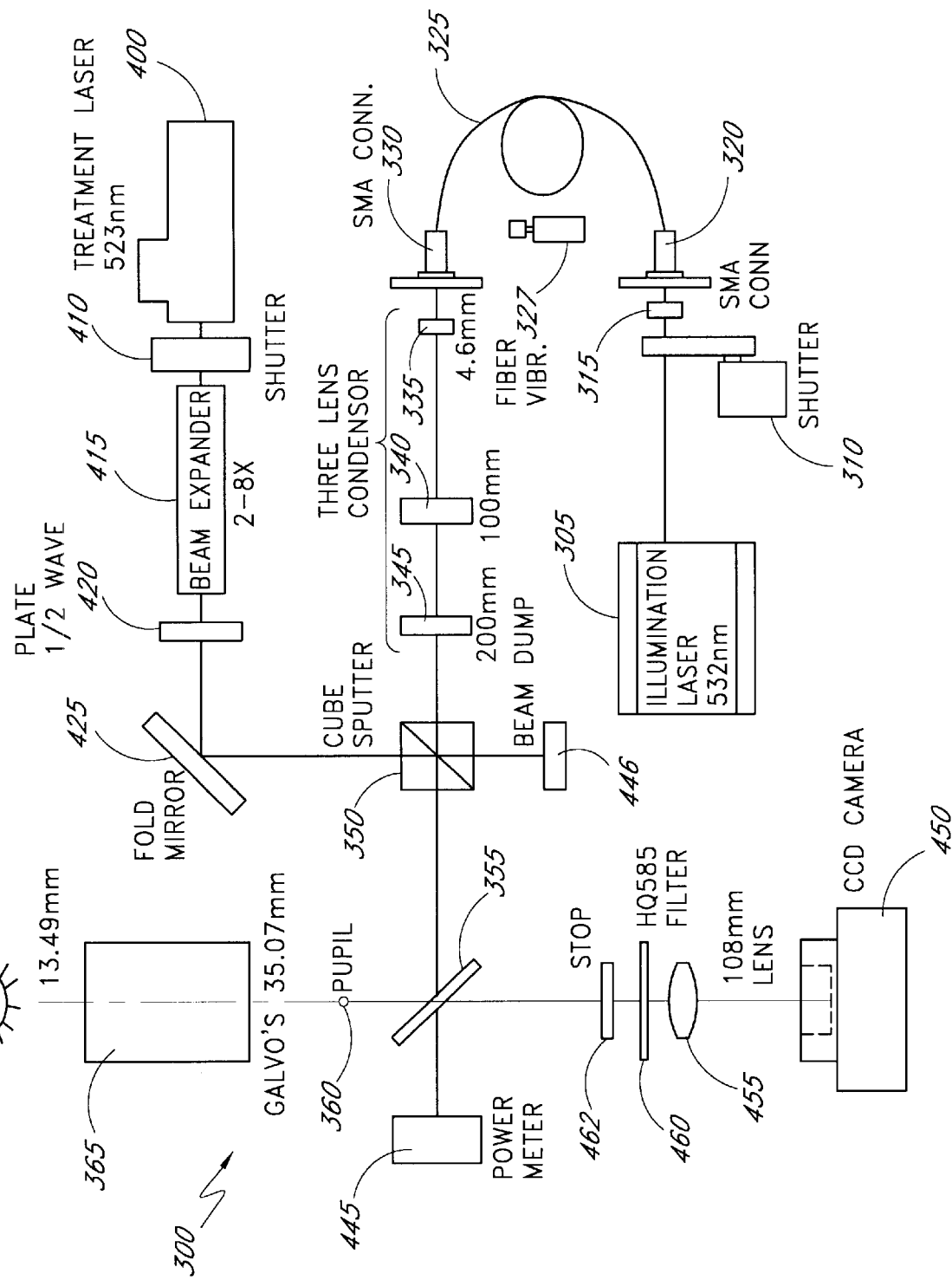
FIG. 3 is a block diagram of the optical subassembly design within one embodiment of a cell treatment apparatus.

FIG. 3 provides a layout of one embodiment of an optical subassembly design 300 within an embodiment of a cell treatment apparatus 10. As illustrated, an illumination laser 305 provides a directed laser output that is used to excite a particular label that is attached to targeted cells within the specimen. In this embodiment, the illumination laser emits light at a wavelength of 532 nm. Once the illumination laser has generated a light beam, the light passes into a shutter 310 which controls the pulse length of the laser light.

After the illumination laser light passes through the shutter 310, it enters a ball lens 315 where it is focused into an SMA fiber optic connector 320. After the illumination laser beam has entered the fiber optic connector 320, it is transmitted through a fiber optic cable 325 to an outlet 330. By passing the illumination beam through the fiber optic cable 325, the illumination laser 305 can be positioned anywhere within the treatment apparatus and thus is not limited to only being positioned within a direct light pathway to the optical components. In one embodiment, the fiber optic cable 325 is connected to a vibrating motor 327 for the purpose of mode scrambling and generating a more uniform illumination spot.

After the light passes through the outlet 330, it is directed into a series of condensing lenses in order to focus the beam to the proper diameter for illuminating one frame of cells. As used herein, one frame of cells is defined as the portion of the biological specimen that is captured within one frame image captured by the camera. This is described more specifically below.

Accordingly, the illumination laser beam passes through a first condenser lens 335. In one embodiment, this first lens has a focal length of 4.6 mm. The light beam then passes through a second condenser lens 340 which, in one embodiment, provides a 100 mm focal length. Finally, the light beam passes into a third condenser lens 345, which preferably provides a 200 mm focal length. While the present invention has been described using specific condenser lenses, it should be apparent that other similar lens configurations that focus the illumination laser beam to an advantageous diameter would function similarly. Thus, this invention is not limited to the specific implementation of any particular condenser lens system.

Once the illumination laser beam passes through the third condenser lens 345, it enters a cube beamsplitter 350 that is designed to transmit the 532 nm wavelength of light emanating from the illumination laser. Preferably, the cube beamsplitter 350 is a 25.4 mm square cube (Melles-Griot, Irvine, Calif.). However, other sizes are anticipated to function similarly. In addition, a number of plate beamsplitters or pellicle beamsplitters could be used in place of the cube beamsplitter 350 with no appreciable change in function.

Once the illumination laser light has been transmitted through the cube beamsplitter 350, it reaches a long wave pass mirror 355 that reflects the 532 nm illumination laser light to a set of galvanometer mirrors 360 that steer the illumination laser light under computer control through a scanning lens (Special Optics, Wharton, N.J.) 365 to the specimen (not shown). The galvanometer mirrors are controlled so that the illumination laser light is directed at the proper cell population (i.e. frame of cells) for imaging.

The light from the illumination laser is of a wavelength that is useful for illuminating the specimen. In this embodiment, energy from a continuous wave 532 nm Nd:YAG frequency-doubled laser (B&W Tek, Newark, Del.) reflects off the long wave pass mirror (Custom Scientific, Phoenix, Ariz.) and excites fluorescent tags in the specimen. In one embodiment, the fluorescent tag is phycoerythrin. Alternatively, Alexa 532 (Molecular Probes, Eugene, Oreg.) can be used. Phycoerythrin and Alexa 532 have emission spectra with peaks near 580 nm, so that the emitted fluorescent light from the specimen is transmitted via the long wave pass mirror to be directed into the camera. The use of the filter in front of the camera blocks light that is not within the wavelength range of interest, thereby reducing the amount of background light entering the camera.

It is generally known that many other devices could be used in this manner to illuminate the specimen, including, but not limited to, an arc lamp (e.g., mercury, xenon, etc.) with or without filters, a light-emitting diode (LED), other types of lasers, etc. Advantages of this particular laser include high intensity, relatively efficient use of energy, compact size, and minimal heat generation. It is also generally known that other fluorochromes with different excitation and emission spectra could be used in such an apparatus with the appropriate selection of illumination source, filters, and long and/or short wave pass mirrors. For example, allophycocyanin (APC) could be excited with a 633 nm HeNe illumination laser, and fluoroisothiocyanate (FITC) could be excited with a 488 nm Argon illumination laser. One skilled in the art could propose many other optical layouts with various components in order to achieve the objective of this invention.

In addition to the illumination laser 305, a treatment laser 400 is present to irradiate the targeted cells once they have been identified by image analysis. Of course, in one embodiment, the treatment induces necrosis of targeted cells within the cell population. As shown, the treatment laser 400 outputs an energy beam of 523 nm that passes through a shutter 410. Although the exemplary laser outputs an energy beam having a 523 nm wavelength, other sources that generate energy at other wavelengths are also within the scope of the present invention.

Once the treatment laser energy beam passes through the shutter 410, it enters a beam expander (Special Optics, Wharton, N.J.) 415 which adjusts the diameter of the energy beam to an appropriate size at the plane of the specimen. Following the beam expander 415 is a half-wave plate 420 which controls the polarization of the beam. The treatment laser energy beam is then reflected off a mirror 425 and enters the cube beamsplitter 350. The treatment laser energy beam is reflected by 90° in the cube beamsplitter 350, such that it is aligned with the exit pathway of the illumination laser light beam. Thus, the treatment laser energy beam and the illumination laser light beam both exit the cube beamsplitter 350 along the same light path. From the cube beamsplitter 350, the treatment laser beam reflects off the long wave pass mirror 355, is steered by the galvanometers 360, thereafter enters the scanning lens 365, and finally is focused upon a targeted cell within the specimen.

It should be noted that a small fraction of the illumination laser light beam passes through the long wave pass mirror 355 and enters a power meter sensor (Gentec, Palo Alto, Calif.) 445. The fraction of the beam entering the power sensor 445 is used to calculate the level of power emanating from the illumination laser 305. In an analogous fashion, a small fraction of the treatment laser energy beam passes through the cube beamsplitter 350 and enters a second power meter sensor (Gentec, Palo Alto, Calif.) 446. The fraction of the beam entering the power sensor 446 is used to calculate the level of power emanating from the treatment laser 400. The power meter sensors are electrically linked to the computer system so that instructions/commands within the computer system capture the power measurement and determine the amount of energy that was emitted.

The energy beam from the treatment laser is of a wavelength that is useful for achieving a response in the cells. In the example shown, a pulsed 523 nm Nd:YLF frequency-doubled laser is used to heat a localized volume containing the targeted cell, such that it is induced to die within a pre-determined period of time. The mechanism of death is dependent upon the actual temperature achieved in the cell, as reviewed by Niemz (Niemz 1996).

A Nd:YLF frequency-doubled, solid-state laser (Spectra-Physics, Mountain View, Calif.) is used because of its stability, high repetition rate of firing, and long time of maintenance-free service. However, most cell culture fluids and cells are relatively transparent to light in this green wavelength, and therefore a very high fluence of energy would be required to achieve cell death. To significantly reduce the amount of energy required, and therefore the cost and size of the treatment laser, a dye is purposefully added to the specimen to efficiently absorb the energy of the treatment laser in the specimen. In the example shown, the non-toxic dye FD&C red #40 (allura red) is used to absorb the 523 nm energy from the treatment laser, but one skilled in the art could identify other laser/dye combinations that would result in efficient absorption of energy by the specimen. For example, a 633 nm HeNe laser's energy would be efficiently absorbed by FD&C green #3 (fast green FCF), a 488 nm Argon laser's energy would be efficiently absorbed by FD&C yellow #5 (sunset yellow FCF), and a 1064 nm Nd:YAG laser's energy would be efficiently absorbed by Filtron (Gentex, Zeeland, Mich.) infrared absorbing dye. Through the use of an energy absorbing dye, the amount of energy required to kill a targeted cell can be reduced since more of the treatment laser energy is absorbed in the presence of such a dye.

Another method of achieving thermal killing of cells without the addition of a dye involves the use of an ultraviolet laser. Energy from a 355 nm Nd:YAG frequency-tripled laser will be absorbed by nucleic acids and proteins within the cell, resulting in thermal heating and death. Yet another method of achieving thermal killing of cells without the addition of a dye involves the use of a near-infrared laser. Energy from a 2100 nm Ho:YAG laser or a 2940 nm Er:YAG laser will be absorbed by water within the cell, resulting in thermal heating and death.

Although this embodiment describes the killing of cells via thermal heating by the energy beam, one skilled in the art would recognize that other responses can also be induced in the cells by an energy beam, including photomechanical disruption, photodissociation, photoablation, and photochemical reactions, as reviewed by Niemz (Niemz 1996). Also, a photosensitive substance (e.g., hemtoporphyrin derivative, tin-etiopurpurin, lutetuim texaphyrin) (Oleinick and Evans 1998) within the cell mixture could be specifically activated in targeted cells by irradiation. Additionally, a small, transient pore could be made in the cell membrane (Palumbo et al. 1996) to allow the entry of genetic or other material. Further, specific molecules in or on the cell, such as proteins or genetic material, could be inactivated by the directed energy beam (Grate and Wilson 1999; Jay 1988). These mechanisms of inducing a response in a targeted cell via the use of electromagnetic radiation directed at specific targeted cells are also intended to be incorporated into the present invention.

In addition to the illumination laser 305 and treatment laser 400, the apparatus includes a camera 450 that captures images (i.e. frames) of the cell populations. As illustrated in FIG. 3, the camera 450 is focused through a lens 455 and filter 460 in order to accurately record an image of the cells without capturing stray background images. A stop 462 is positioned between the filter 460 and mirror 355 in order to eliminate light that may enter the camera from angles not associated with the image from the specimen. The filter 460 is chosen to only allow passage of light within a certain wavelength range. This wavelength range includes light that is emitted from the targeted cells upon excitation by the illumination laser 305, as well as light from a back-light source 475.

The back-light source 475 is located above the specimen to provide back-illumination of the specimen at a wavelength different from that provided by the illumination laser 305. This LED generates light at 590 nm, such that it can be transmitted through the long wave pass mirror to be directed into the camera. This back-illumination is useful for imaging cells when there are no fluorescent targets within the frame being imaged. An example of the utility of this back-light is its use in attaining proper focus of the system, even when there are only unstained, non-fluorescent cells in the frame. In one embodiment, the back-light is mounted on the underside of the access door 35 (FIG. 2).

Thus, as discussed above, the only light returned to the camera is from wavelengths that are of interest in the specimen. Other wavelengths of light do not pass through the filter 460, and thus do not become recorded by the camera 450. This provides a more reliable mechanism for capturing images of only those cells of interest. It is readily apparent to one skilled in the art that the single filter 460 could be replaced by a movable filter wheel that would allow different filters to be moved in and out of the optical pathway. In such an embodiment, images of different wavelengths of light could be captured at different times during cell processing, allowing the use of multiple cell labels.

It should be noted that in this embodiment, the camera is a charge-coupled device (CCD) and transmits images back to the computer system for processing. As will be described below, the computer system determines the coordinates of the targeted cells in the specimen by reference to the image captured by the CCD camera.

Figure 4:
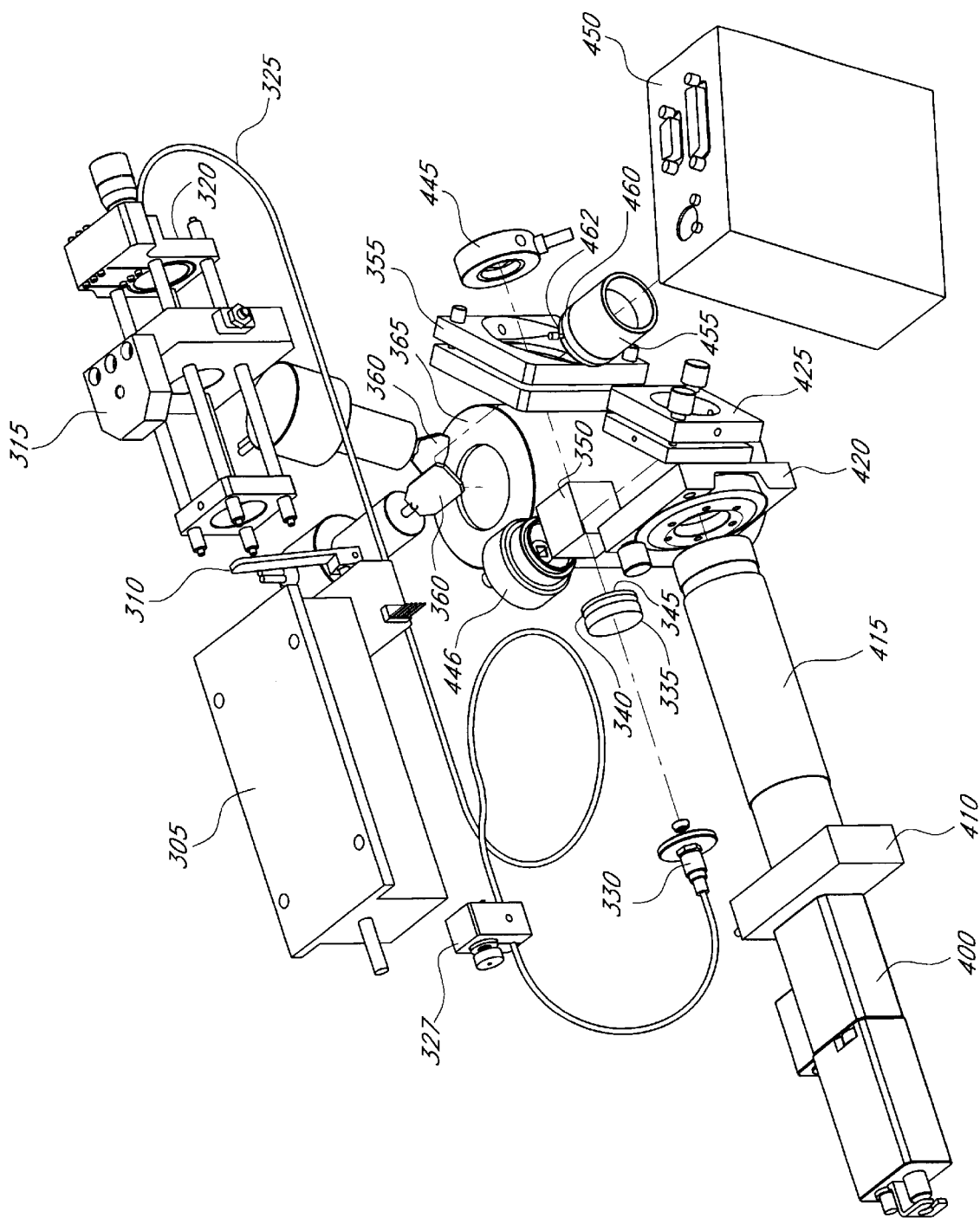
FIG. 4 is a perspective view of one embodiment of an optical subassembly within one embodiment of a cell treatment apparatus.

Referring now to FIG. 4, a perspective view of an embodiment of an optical subassembly is illustrated. As illustrated, the illumination laser 305 sends a light beam through the shutter 310 and ball lens 315 to the SMA fiber optic connector 320. The light passes through the fiber optic cable 325 and through the output 330 into the condenser lenses 335, 340 and 345. The light then enters the cube beamsplitter 350 and is transmitted to the long wave pass mirror 355. From the long wave pass mirror 355, the light beam enters the computer-controlled galvanometers 360 and is then steered to the proper frame of cells in the specimen through the scanning lens 365.

As also illustrated in the perspective drawing of FIG. 4, the treatment laser 400 transmits energy through the shutter 410 and into the beam expander 415. Energy from the treatment laser 400 passes through the beam expander 415 and passes through the half-wave plate 420 before hitting the fold mirror 425, entering the cube beamsplitter 350 where it is reflected 90° to the long wave pass mirror 355, from which it is reflected into the computer controlled galvanometer mirrors 360. After being steered by the galvanometer mirrors 360 through the scanning lens 365, the laser energy beam strikes the proper location within the cell population in order to induce a response in a particular targeted cell.

Figure 5:
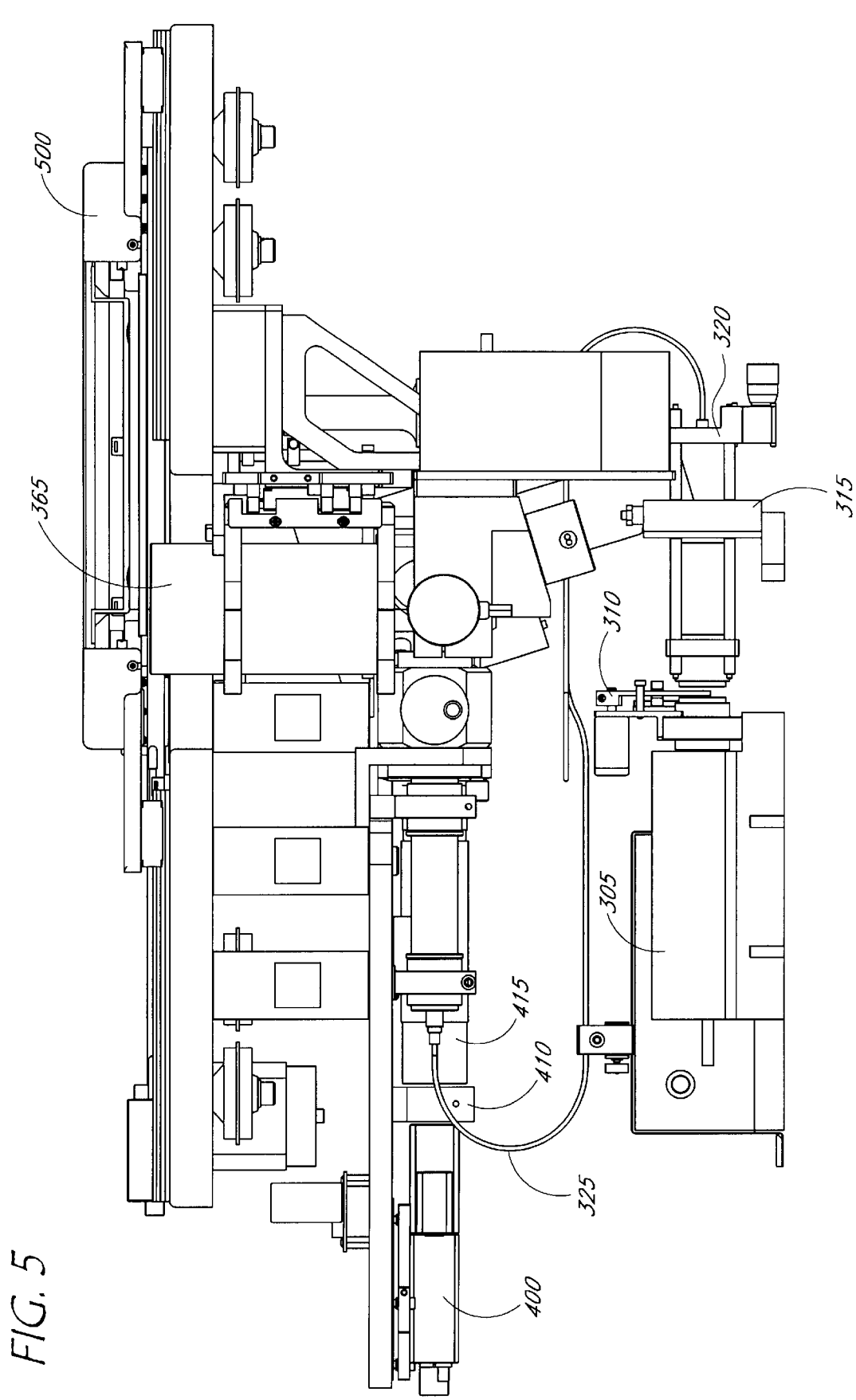
FIG. 5 is a side view of one embodiment of an optical subassembly that illustrates the arrangement of the scanning lens and the movable stage.

In order to accommodate a very large surface area of specimen to treat, the apparatus includes a movable stage that mechanically moves the specimen container with respect to the scanning lens. Thus, once a specific subpopulation (i.e. field) of cells within the scanning lens field-of-view has been treated, the movable stage brings another sub-population of cells within the scanning lens field-of-view. As illustrated in FIG. 5, a computer-controlled movable stage 500 holds a specimen container (not shown) to be processed. The movable stage 500 is moved by computer-controlled servo motors along two axes so that the specimen container can be moved relative to the optical components of the instrument. The stage movement along a defined path is coordinated with other operations of the apparatus. In addition, specific coordinates can be saved and recalled to allow return of the movable stage to positions of interest. Encoders on the x and y movement provide closed-loop feedback control on stage position.

Figure 6:
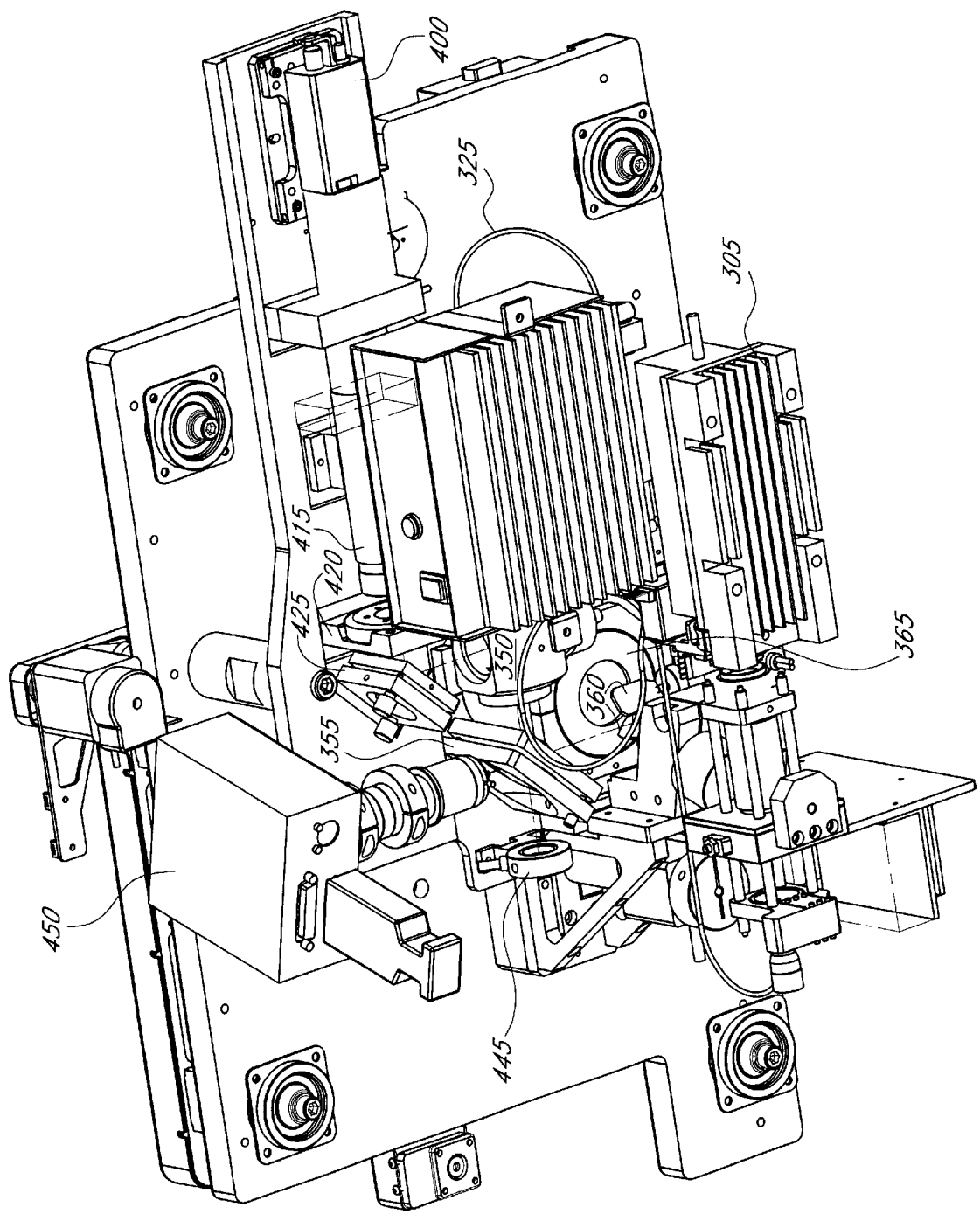
FIG. 6 is a bottom perspective view of one embodiment of an optical subassembly.

The flat-field (F-theta) scanning lens 365 is mounted below the movable stage. The scanning lens field-of-view comprises the portion of the specimen that is presently positioned above the scanning lens by the movable stage 500. The lens 365 is mounted to a stepper motor that allows the lens 365 to be automatically raised and lowered (along the z-axis) for the purpose of focusing the system. As illustrated in FIGS. 4–6, below the scanning lens 365 are the galvanometer-controlled steering mirrors 360 that deflect electromagnetic energy along two perpendicular axes. Behind the steering mirrors is the long wave pass mirror 355 that reflects electromagnetic energy of a wavelength shorter than 545 nm. Wavelengths longer than 545 nm are passed through the long wave pass mirror, directed through the filter 460, coupling lens 455, and into the CCD camera, thereby producing an image of the appropriate size on the CCD sensor of the camera 450 (See FIGS. 3 and 4). The magnification defined by the combination of the scanning lens 365 and coupling lens 455 is chosen to reliably detect single cells while maximizing the area viewed in one frame by the camera. Although a CCD camera (DVC, Austin, Tex.) is illustrated in this embodiment, the camera can be any type of detector or image gathering equipment known to those skilled in the art. The optical subassembly of the apparatus is preferably mounted on a vibration-isolated platform to provide stability during operation as illustrated in FIGS. 2 and 5.

Figure 7:
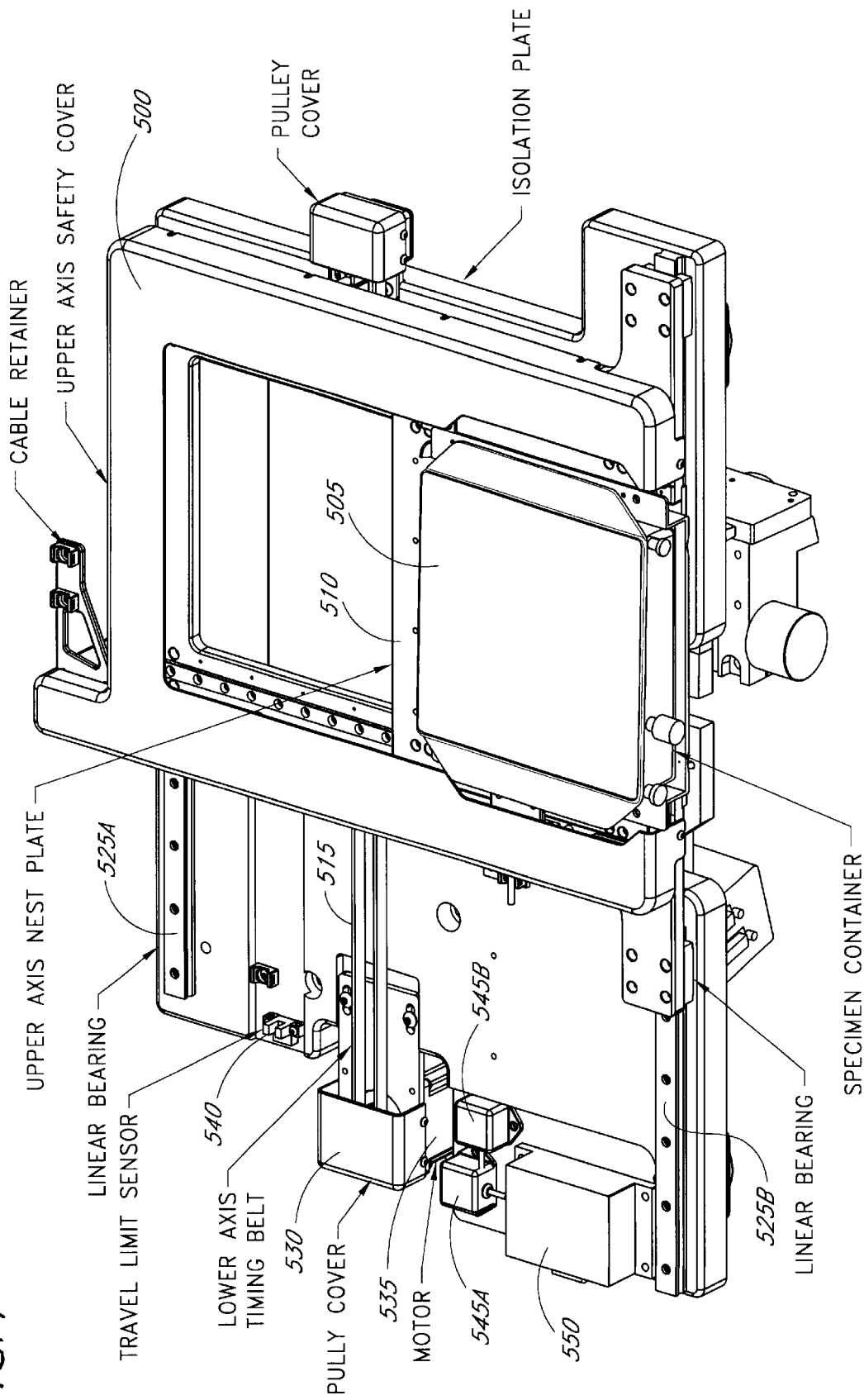
FIG. 7 is a top perspective view of the movable stage of the cell treatment apparatus.

Referring now to FIG. 7, a top view of the movable stage 500 is illustrated. As shown, a specimen container is mounted in the movable stage 500. The specimen container 505 rests on an upper axis nest plate 510 that is designed to move in the forward/backward direction with respect to the movable stage 500. A stepper motor (not shown) is connected to the upper axis nest plate 510 and computer system so that commands from the computer cause forward/backward movement of the specimen container 505.

The movable stage 500 is also connected to a timing belt 515 that provides side-to-side movement of the movable stage 500 along a pair of bearing tracks 525A,B. The timing belt 515 attaches to a pulley (not shown) housed under a pulley cover 530. The pulley is connected to a stepper motor 535 that drives the timing belt 515 to result in side-to-side movement of the movable stage 500. The stepper motor 535 is electrically connected to the computer system so that commands within the computer system result in side-to-side movement of the movable stage 500. A travel limit sensor 540 connects to the computer system and causes an alert if the movable stage travels beyond a predetermined lateral distance.

A pair of accelerometers 545A,B is preferably incorporated on this platform to register any excessive bumps or vibrations that may interfere with the apparatus operation. In addition, a two-axis inclinometer 550 is preferably incorporated on the movable stage to ensure that the specimen container is level, thereby reducing the possibility of gravity-induced motion in the specimen container.

The specimen chamber has a fan with ductwork to eliminate condensation on the specimen container, and a thermocouple to determine whether the specimen chamber is within an acceptable temperature range. Additional fans are provided to expel the heat generated by the electronic components, and appropriate filters are used on the air intakes 215A,B.

The computer system 225 controls the operation and synchronization of the various pieces of electronic hardware described above. The computer system can be any commercially available computer that can interface with the hardware. One example of such a computer system is an Intel Pentium II-based computer running the Microsoft Windows® NT operating system. Software is used to communicate with the various devices, and control the operation in the manner that is described below.

When the apparatus is first initialized, the computer loads files from the hard drive into RAM for proper initialization of the apparatus. A number of built-in tests are automatically performed to ensure the apparatus is operating properly, and calibration routines are executed to calibrate the cell treatment apparatus. Upon successful completion of these routines, the user is prompted to enter information via the keyboard and mouse regarding the procedure that is to be performed (e.g. patient name, ID number, etc.). Once the required information is entered, the user is prompted to open the access door 35 and load a specimen onto the movable stage.

Once a specimen is in place on the movable stage and the door is closed, the computer passes a signal to the stage to move into a home position. The fan is initialized to begin warming and defogging of the specimen. During this time, cells within the specimen are allowed to settle to the bottom surface. In addition, during this time, the apparatus may run commands that ensure that the specimen is properly loaded, and is within the focal range of the system optics. For example, specific markings on the specimen container can be located and focused on by the system to ensure that the scanning lens has been properly focused on the bottom of the specimen container. After a suitable time, the computer turns off the fan to prevent excess vibrations during treatment, and cell treatment processing begins.

First, the computer instructs the movable stage to be positioned over the scanning lens so that the first area (i.e. field) of the specimen to be treated is directly in the scanning lens field-of-view. The galvanometer mirrors are instructed to move such that the center frame within the field-of-view is imaged in the camera. As discussed below, the field imaged by the scanning lens is separated into a plurality of frames. Each frame is the proper size so that the cells within the frame are effectively imaged by the camera.

The back-light 475 is then activated in order to illuminate the field-of-view so that it can be brought into focus by the scanning lens. Once the scanning lens has been properly focused upon the specimen, the computer system divides the field-of-view into a plurality of frames so that each frame is analyzed separately by the camera. This methodology allows the apparatus to process a plurality of frames within a large field-of-view without moving the mechanical stage. Because the galvanometers can move from one frame to the next very rapidly compared to the mechanical steps involved in moving the stage, this method results is an extremely fast and efficient apparatus.

In one preferred embodiment, the apparatus described herein processes at least 1, 2, 3, 4, 5, 6, or 7 square centimeters of a biological specimen per minute. In another embodiment, the apparatus described herein processes at least 0.25, 0.5, 1, 2, 3 or 4 million cells of a biological specimen per minute. In one other embodiment, the apparatus can preferably induce a response in targeted cells at a rate of 50, 100, 150, 200, 250, 300, 350, or 400 cells per second.

Initially, an image of the frame at the center of the field-of-view is captured by the camera and stored to a memory in the computer. Instructions in the computer analyze the focus of the specimen by looking at the size of, number of, and other object features in the image. If necessary, the computer instructs the z-axis motor attached to the scanning lens to raise or lower in order to achieve the best focus. The apparatus may iteratively analyze the image at several z-positions until the best focus is achieved. The galvanometer-controlled mirrors are then instructed to image a first frame, within the field-of-view, in the camera. For example, the entire field-of-view might be divided into 4, 9, 12, 18, 24 or more separate frames that will be individually captured by the camera. Once the galvanometer mirrors are pointed to the first frame in the field-of-view, the shutter in front of the illumination laser is opened to illuminate the first frame through the galvanometer mirrors and scanning lens. The camera captures an image of any fluorescent emission from the specimen in the first frame of cells. Once the image has been acquired, the shutter in front of the illumination laser is closed and a software program (Epic, Buffalo Grove, Ill.) within the computer processes the image.

The power sensor 445 discussed above detects the level of light that was emitted by the illumination laser, thereby allowing the computer to calculate if it was adequate to illuminate the frame of cells. If not, another illumination and image capture sequence is performed. Repeated failure to sufficiently illuminate the specimen will result in an error condition that is communicated to the operator.

Shuttering of illumination light reduces undesirable heating and photobleaching of the specimen and provides a more repeatable fluorescent signal. An image analysis algorithm is run to locate the x-y centroid coordinates of all targeted cells in the frame by reference to features in the captured image. If there are targets in the image, the computer calculates the two-dimensional coordinates of all target locations in relation to the movable stage position and field-of-view, and then positions the galvanometer-controlled mirrors to point to the location of the first target in the first frame of cells. It should be noted that only a single frame of cells within the field-of-view has been captured and analyzed at this point. Thus, there should be a relatively small number of identified targets within this sub-population of the specimen. Moreover, because the camera is pointed to a smaller population of cells, a higher magnification is used so that each target is imaged by many pixels within the CCD camera.

Once the computer system has positioned the galvanometer controlled mirrors to point to the location of the first targeted cell within the first frame of cells, the treatment laser is fired for a brief interval so that the first targeted cell is given an appropriate dose of energy. The power sensor 446 discussed above detects the level of energy that was emitted by the treatment laser, thereby allowing the computer to calculate if it was adequate to induce a response in the targeted cell. If not sufficient, the treatment laser is fired at the same target again. If repeated shots do not deliver the required energy dose, an error condition is communicated to the operator. These targeting, firing, and sensing steps are repeated by the computer for all targets identified in the captured frame.

Once all of the targets have been irradiated with the treatment laser in the first frame of cells, the mirrors are then positioned to the second frame of cells in the field-of-view, and the processing repeats at the point of frame illumination and camera imaging. This processing continues for all frames within the field-of-view above the scanning lens. When all of these frames have been processed, the computer instructs the movable stage to move to the next field-of-view in the specimen, and the process repeats at the back-light illumination and auto-focus step. Frames and fields-of-view are appropriately overlapped to reduce the possibility of inadvertently missing areas of the specimen. Once the specimen has been fully processed, the operator is signaled to remove the specimen, and the apparatus is immediately ready for the next specimen.

Although the text above describes the analysis of fluorescent images for locating targets, one can easily imagine that the non-fluorescent back-light LED illumination images will be useful for locating other types of targets as well, even if they are unlabeled.

The advantage of using the galvanometer mirrors to control the imaging of successive frames and the irradiation of successive targets is significant. One brand of galvanometer is the Cambridge Technology, Inc. model number 6860 (Cambridge, Mass.). This galvanometer can reposition very accurately within a few milliseconds, making the processing of large areas and many targets possible within a reasonable amount of time. In contrast, the movable stage is relatively slow, and is therefore used only to move specified areas of the specimen into the scanning lens field-of-view. Error signals continuously generated by the galvanometer control boards are monitored by the computer to ensure that the mirrors are in position and stable before an image is captured, or before a target is fired upon, in a closed-loop fashion.

In the context of the present invention, the term "specimen" has a broad meaning. It is intended to encompass any type of biological sample placed within the apparatus. The specimen may be enclosed by, or associated with, a container to maintain the sterility and viability of the cells. Further, the specimen may incorporate, or be associated with, a cooling apparatus to keep it above or below ambient temperature during operation of the methods described herein. The specimen container, if one is used, must be compatible with the use of the illumination laser, back-light illuminator, and treatment laser, such that it transmits adequate energy without being substantially damaged itself.

Of course, many variations of the above-described embodiment are possible, including alternative methods for illuminating, imaging, and targeting the cells. For example, movement of the specimen relative to the scanning lens could be achieved by keeping the specimen substantially stationary while the scanning lens is moved. Steering of the illumination beam, images, and energy beam could be achieved through any controllable reflective or diffractive device, including prisms, piezo-electric tilt platforms, or acousto-optic deflectors. Additionally, the apparatus can image/process from either below or above the specimen. Because the apparatus is focused through a movable scanning lens, the illumination and energy beams can be directed to different focal planes along the z-axis. Thus, portions of the specimen that are located at different vertical heights can be specifically imaged and processed by the apparatus in a three-dimensional manner. The sequence of the steps could also be altered without changing the process. For example, one might locate and store the coordinates of all targets in the specimen, and then return to the targets to irradiate them with energy one or more times over a period of time.

To optimally process the specimen, it should be placed on a substantially flat surface so that a large portion of the specimen appears within a narrow range of focus, thereby reducing the need for repeated auto-focus steps. The density of cells on this surface can, in principle, be at any value. However, the cell density should be as high as possible to minimize the total surface area required for the procedure.

The following examples illustrate the use of the described method and apparatus in different applications.

EXAMPLE 1

Autologous HSC Transplantation

A patient with a B cell-derived metastatic tumor in need of an autologous HSC transplant is identified by a physician. As a first step in the treatment, the patient undergoes a standard HSC harvest procedure, resulting in collection of approximately $1\times10^{10}$ hematopoietic cells with an unknown number of contaminating tumor cells. The harvested cells are enriched for HSC by a commercial immunoaffinity column (Isolex® 300, Nexell Therapeutics, Irvine, Calif.) that selects for cells bearing the CD34 surface antigen, resulting in a population of approximately $3\times10^8$ hematopoietic cells, with an unknown number of tumor cells. The mixed population is thereafter contacted with anti-B cell antibodies (directed against CD20 and CD22) that are conjugated to phycoerythrin. The labeled antibodies specifically bind to the B cell-derived tumor cells.

The mixed cell population is then placed in a sterile specimen container on a substantially flat surface near confluence, at approximately 500,000 cells per square centimeter. The specimen is placed on the movable stage of the apparatus described above, and all detectable tumor cells are identified by reference to phycoerythrin and targeted with a lethal dose of energy from a treatment laser. The design of the apparatus allows the processing of a clinical-scale transplant specimen in under 4 hours. The cells are recovered from the specimen container, washed, and then cryopreserved. Before the cells are reinfused, the patient is given high-dose chemotherapy to destroy the tumor cells in the patient's body. Following this treatment, the processed cells are thawed at 37° C. and are given to the patient intravenously. The patient subsequently recovers with no remission of the original cancer.

EXAMPLE 2

Allogeneic HSC Transplantation

In another embodiment, the significant risk and severity of graft-versus-host disease in the allogeneic HSC transplant setting can be combated. A patient is selected for an allogeneic transplant once a suitable donor is found. Cells are harvested from the selected donor as described in the above example. In this case, the cell mixture is contacted with phycoerythrin-labeled anti-CD3 T-cell antibodies. Alternatively, specific allo-reactive T-cell subsets could be labeled using an activated T-cell marker (e.g. CD69) in the presence of allo-antigen. The cell population is processed by the apparatus described herein, thereby precisely defining and controlling the number of T-cells given to the patient. This type of control is advantageous, because administration of too many T-cells increases the risk of graft-versus-host disease, whereas too few T-cells increases the risk of graft failure and the risk of losing of the known beneficial graft-versus-leukemia effect. The present invention and methods are capable of precisely controlling the number of T-cells in an allogeneic transplant.

EXAMPLE 3

Tissue Engineering

In another application, the present apparatus is used to remove contaminating cells in inocula for tissue engineering applications. Cell contamination problems exist in the establishment of primary cell cultures required for implementation of tissue engineering applications, as described by Langer and Vacanti (Langer and Vacanti 1999). In particular, chondrocyte therapies for cartilage defects are hampered by impurities in the cell populations derived from cartilage biopsies. Accordingly, the present invention is used to specifically remove these types of cells from the inocula.

For example, a cartilage biopsy is taken from a patient in need of cartilage replacement. The specimen is then grown under conventional conditions (Brittberg et al. 1994). The culture is then stained with a specific label for any contaminating cells, such as fast-growing fibroblasts. The cell mixture is then placed within the apparatus described and the labeled, contaminating cells are targeted by the treatment laser, thereby allowing the slower growing chondrocytes to fully develop in culture.

EXAMPLE 4

Stem Cell Therapy

Yet another embodiment involves the use of embryonic stem cells to treat a wide variety of diseases. Since embryonic stem cells are undifferentiated, they can be used to generate many types of tissue that would find use in transplantation, such as cardiomyocytes and neurons. However, undifferentiated embryonic stem cells that are implanted can also lead to a jumble of cell types which form a type of tumor known as a teratoma (Pedersen 1999). Therefore, therapeutic use of tissues derived from embryonic stem cells must include rigorous purification of cells to ensure that only sufficiently differentiated cells are implanted. The apparatus described herein is used to eliminate undifferentiated stem cells prior to implantation of embryonic stem cell-derived tissue in the patient.

EXAMPLE 5

Generation of Human Tumor Cell Cultures

In another embodiment, a tumor biopsy is removed from a cancer patient for the purpose of initiating a culture of human tumor cells. However, the in vitro establishment of primary human tumor cultures from many tumor types is complicated by the presence of contaminating primary cell populations that have superior in vitro growth characteristics over tumor cells. For example, contaminating fibroblasts represent a major challenge in establishing many cancer cell cultures. The disclosed apparatus is used to particularly label and destroy the contaminating cells, while leaving the biopsied tumor cells intact. Accordingly, the more aggressive primary cells will not overtake and destroy the cancer cell line.

EXAMPLE 6

Generation of a Specific mRNA Expression Library

The specific expression pattern of genes within different cell populations is of great interest to many researchers, and many studies have been performed to isolate and create libraries of expressed genes for different cell types. For example, knowing which genes are expressed in tumor cells versus normal cells is of great potential value (Cossman et al. 1999). Due to the amplification methods used to generate such libraries (e.g. PCR), even a small number of contaminating cells will result in an inaccurate expression library (Cossman et al. 1999; Schutze and Lahr 1998). One approach to overcome this problem is the use of laser capture microdissection (LCM), in which a single cell is used to provide the starting genetic material for amplification (Schutze, Lahr 1998). Unfortunately, gene expression in single cells is somewhat stochastic, and may be biased by the specific state of that individual cell at the time of analysis (Cossman et al. 1999). Therefore, accurate purification of a significant cell number prior to extraction of mRNA would enable the generation of a highly accurate expression library, one that is representative of the cell population being studied, without biases due to single cell expression or expression by contaminating cells. The methods and apparatus described in this invention can be used to purify cell populations so that no contaminating cells are present during an RNA extraction procedure.

EXAMPLE 7

Transfection of a Specific Cell Population

Many research and clinical gene therapy applications are hampered by the inability to transfect an adequate number of a desired cell type without transfecting other cells that are present. The method of the present invention would allow selective targeting of cells to be transfected within a mixture of cells. By generating a photomechanical shock wave at or near a cell membrane with a targeted energy source, a transient pore can be formed, through which genetic (or other) material can enter the cell. This method of gene transfer has been called optoporation (Palumbo et al. 1996). The apparatus described above can achieve selective optoporation on only the cells of interest in a rapid, automated, targeted manner.

For example, white blood cells are plated in a specimen container having a solution containing DNA to be transfected. Fluorescently-labeled antibodies having specificity for stem cells are added into the medium and bind to the stem cells. The specimen container is placed within the cell processing apparatus and a treatment laser is targeted to any cells that become fluorescent under the illumination laser light. The treatment laser facilitates transfection of DNA specifically into the targeted cells.

EXAMPLE 8

Selection of Desirable Clones in a Biotechnology Application

In many biotechnology processes where cell lines are used to generate a valuable product, it is desirable to derive clones that are very efficient in producing the product. This selection of clones is often carried out manually, by inspecting a large number of clones that have been isolated in some manner. The present invention would allow rapid, automated inspection and selection of desirable clones for production of a particular product. For example, hybridoma cells that are producing the greatest amounts of antibody can be identified by a fluorescent label directed against the $F_c$ region. Cells with no or dim fluorescent labeling are targeted by the treatment laser for killing, leaving behind the best producing clones for use in antibody production.

EXAMPLE 9

Automated Monitoring of Cellular Responses

Automated monitoring of cellular responses to specific stimuli is of great interest in high-throughput drug screening. Often, a cell population in one well of a well-plate is exposed to a stimulus, and a fluorescent signal is then captured over time from the cell population as a whole. Using the methods and apparatus described herein, more detailed monitoring could be done at the single cell level. For example, a cell population can be labeled to identify a characteristic of a subpopulation of cells that are of interest. This label is then excited by the illumination laser to identify those cells. Thereafter, the treatment laser is targeted at the individual cells identified by the first label, for the purpose of exciting a second label, thereby providing information about each cell's response. Since the cells are substantially stationary on a surface, each cell could be evaluated multiple times, thereby providing temporal information about the kinetics of each cell's response. Also, through the use of the large area scanning lens and galvanometer mirrors, a relatively large number of wells could be quickly monitored over a short period of time.

As a specific example, consider the case of alloreactive T-cells as presented in Example 2 above. In the presence of allo-antigen, activated donor T-cells could be identified by CD69. Instead of using the treatment laser to target and kill these cells, the treatment laser could be used to examine the intracellular pH of every activated T-cell through the excitation and emitted fluorescence of carboxyfluorescein diacetate. The targeted laser allows the examination of only cells that are activated, whereas most screening methods evaluate the response of an entire cell population. If a series of such wells are being monitored in parallel, various agents could be added to individual wells, and the specific activated T-cell response to each agent could be monitored over time. Such an apparatus would provide a high-throughput screening method for agents that ameliorate the alloreactive T-cell response in graft-versus-host disease. Based on this example, one skilled in the art could imagine many other examples in which a cellular response to a stimulus is monitored on an individual cell basis, focusing only on cells of interest identified by the first label.

Although aspects of the present invention have been described by particular embodiments exemplified herein, the present invention is not so limited. The present invention is only limited by the claims appended below.

REFERENCES CITED

Andersen, N. S., Donovan, J. W., Borus, J. S., Poor, C. M., Neuberg, D., Aster, J. C., Nadler, L. M., Freedman, A. S., and Gribben, J. G.: Failure of immunologic purging in mantle cell lymphoma assessed by polymerase chain reaction detection in minimal residual disease. *Blood* 90: 4212–4221, 1997

Bird, J. M., Luger, S., Mangan, P., Edelstein, M., Silberstein, L., Powlis, W., Ball, J., Schultz, D. J., and Stadtmauer, E. A.: 4-Hydroperoxycyclophosphamide purged autologous bone marrow transplantation in non-Hodgkin's lymphoma patients at high risk of none marrow involvement. *BMT* 18: 309–313, 1996

Brittberg, M., Lindahl, A., Nilsson, A., Ohlsson, C., Isaksson, O., and Peterson, L.: Treatment of deep cartilage defects in the knee with autologous chondrocyte transplantation. *N.E.J.Med.* 331: 889–895, 1994

Brockstein, B. E., Ross, A. A., Moss, T. J., Kahn, D. G., Hollingsworth, K., and Williams, S. F.: Tumor cell contamination of bone marrow harvest products: Clinical consequences in a cohort of advanced-stage breast cancer patients undergoing high-dose chemotherapy. *J.Hematotherapy* 5: 617–624, 1996

Brugger, W., Bross, K. J., Glatt, M., Weber, F., Mertelsmann, R., and Kanz, L.: Mobilization of tumor cells and hematopoietic progenitor cells into peripheral blood of patients with solid tumors. *Blood* 83: 636–640, 1994

Clarke, M. F., Apel, I. J., Benedict, M. A., Eipers, P. G., Sumantran, V., Gonzalez-Garcia, M., Doedens, M., Fukunaga, N., Davidson, B., Dick, J. E., Minn, A. J., Boise, L. H., Thompson, C. B., Wicha, M., and Nunez, G.: A recombinant bcl-$x_s$ adenovirus selectively induces apoptosis in cancer cells but not in normal bone marrow cells. *PNAS* 92: 1102–11028, 1995

Cossman, J. C., Annunziata, C. M., Barash, S., Staudt, L., Dillon, P., He, W.-W., Ricciardi-Castognoli, P., Rosen, C. A., and Carter, K. C.: Reed-Sternberg cell genome expression supports a B-cell lineage. *Blood* 94: 411–416, 1999

Deisseroth, A. B., Zu, Z., Claxton, D., Hanania, E. G., Fu, S., Ellerson, D., Goldberg, L., Thomas, M., Janicek, K., Anderson, W. F., Hester, J., Korbling, M., Durett, A., Moen, R., Berenson, R., Heimfeld, S., Hamer, J., Calver, L., Tibbits, P., Talpaz, M., Kantarjiam, H., Champlin, R., and Reading, C.: Genetic marking shows that $Ph^+$ cells present in autologous transplants of chronic myelogenous leukemia (CML) contribute to relapse after autologous bone marrow transplantation in CML. *Blood* 83: 3068–3076, 1994

Dooley, D. C., Xiao, M., Wickramasinghe, S. R., Oppenlander, B. K., and Castino, F.: A novel inexpensive technique for the removal of breast cancer cells from mobilized peripheral blood stem cell products. *Blood* 88: 252a, 1996

Fields, K. K., Elfenbein, G. J., Trudeau, W. L., Perkins, J. B., Janssen, W. E., and Moscinski, L. C.: Clinical significance of bone marrow metastases as detected using the polymerase chain reaction in patients with breast cancer undergoing high-dose chemotherapy and autologous bone marrow transplantation. *J.Clin.Oncol.* 14: 1868–1876, 1996

Freedman, A. S., Neuberg, D., Mauch, P., Soiffer, R. J., Anderson, K. C., Fisher, D. C., Schlossman, R., Alyea, E. P., Takvorian, T., Jallow, H., Kuhlman, C., Ritz, J., Nadler, L. M., and Gribben, J. G.: Long-term follow-up of autologous bone marrow transplantation in patients with relapsed follicular lymphoma. *Blood* 94: 3325–3333, 1999

Gazitt, Y., Reading, C. C., Hoffman, R., Wickrema, A., Vesole, D. H., Jagannath, S., Condino, J., Lee, B., Barlogie, B., and Tricot, G.: Purified $CD34^+lin^-Thy^+$ stem cells do not contain clonal myeloma cells. *Blood* 86: 381–389, 1995

Grate, D. and Wilson, C.: Laser-mediated, site-specific inactivation of RNA transcripts. *PNAS* 96: 6131–6136, 1999

Gribben, J. G., Freedman, A. S., Neuberg, D., Roy, D. C., Blake, K. W., Woo, S. D., Grossbard, M. L., Rabinowe, S. N., Coral, F., Freeman, G. J., Ritz, J., and Nadler, L. M.: Immunologic purging of marrow assessed by PCR before autologous bone marrow transplantation for B-cell lymphoma. *N.E.J.Med.* 325: 1525–1533, 1991

Gulati, S. C. and Acaba, L.: Rationale for purging in autologous stem cell transplantation. *J.Hematotherapy* 2: 467–471, 1993

Gulliya, K. S. and Pervaiz, S.: Elimination of clonogenic tumor cells from HL-60, Daudi, and U-937 cell lines by laser photoradiation therapy: Implications for autologous bone marrow purging. *Blood* 73: 1059–1065, 1989

Higuchi, W., Moriyama, Y., Kishi, K., Koike, T., Shibata, A., Shinada, S., Tada, I., and Miura, A.: Hematopoietic recovery in a patient with acute lymphoblastic leukemia after an autologous marrow graft purged by combined hyperthermia and interferon in vitro. *Bone Marrow Transplant.* 7: 163–166, 1991

Jay, D. G.: Selective destruction of protein function by chromophore-assisted laser inactivation. *PNAS* 85: 5454–5458, 1988

Kvalheim, G., Holte, H., Jakobsen, E., and Kvaloy, S.: Immunomagnetic purging of lymphoma cells from autografts. *J.Hematotherapy* 5: 561–562, 1996

Langer, R. S. and Vacanti, J. P.: Tissue engineering: The challenges ahead. *Sci.Am.* 280: 86–89, 1999

Mapara, M. Y., Körner, I. J., Hildebrandt, M., Bargou, R., Krahl, D., Reichardt, P., and Dörken, B.: Monitoring of tumor cell purging after highly efficient immunomagnetic selection of CD34 cells from leukapheresis products in breast cancer patients: Comparison of immunocytochemical tumor cell staining and reverse transcriptase-polymerase chain reaction. *Blood* 89: 337–344, 1997

Mapara, M. Y., Korner, I. J., Lentzsch, S., Krahl, D., Reichardt, P., and Dorken, B.: Combined positive/negative purging and transplantation of peripheral blood progenitor cell autografts in breast cancer patients: A pilot study. *Exp.Hematol.* 27: 169–175, 1999

Niemz, M. H.: Laser-tissue interactions: Fundamentals and applications. Springer-Verlag, Berlin, 1996

Oleinick, N. L. and Evans, H. H.: The photobiology of photodynamic therapy: Cellular targets and mechanisms. *Rad.Res.* 150: S146–S156, 1998

Palumbo, G., Caruso, M., Crescenzi, E., Tecce, M. F., Roberti, G., and Colasanti, A.: Targeted gene transfer in eukaryotic cells by dye-assisted laser optoporation. *J.Photochem.Photobiol.* 36: 41–46, 1996

Paulus, U., Dreger, P., Viehmann, K., von Neuhoff, N., and Schmitz, N.: Purging peripheral blood progenitor cell grafts from lymphoma cells: Quantitative comparison of immunomagnetic CD34+ selection systems. *Stem Cells* 15: 297–304, 1997

Pedersen, R. A.: Embryonic stem cells for medicine. *Sci.Amer.* 280: 68–73, 1999

Rill, D. R., Santana, V. M., Roberts, W. M., Nilson, T., Bowman, L. C., Krance, R. A., Heslop, H. E., Moen, R. C., Ihle, J. N., and Brenner, M. K.: Direct demonstration that autologous bone marrow transplantation for solid tumors can return a multiplicity of tumorigenic cells. *Blood* 84: 380–383, 1994

Robertson, M. J., Soiffer, R. J., Freedman, A. S., Rabinowe, S. L., Anderson, K. C., Ervin, T. J., Murray, C., Dear, K., Griffin, J. D., Nadler, L. M., and Ritz, J.: Human bone marrow depleted of CD33-positive cells mediates delayed but durable reconstitution of hematopoiesis: Clinical trial of MY9 monoclonal antibody-purged autografts for the treatment of acute myeloid leukemia. *Blood* 79: 2229–2236, 1992

Schulze, R., Schulze, M., Wischnik, A., Ehnle, S., Doukas, K., Behr, W., Ehret, W., and Schlimok, G.: Tumor cell contamination of peripheral blood stem cell transplants and bone marrow in high-risk breast cancer patients. *Bone Marrow Transplant.* 19: 1223–1228, 1997

Schutze, K. and Lahr, G.: Identification of expressed genes by laser-mediated manipulation of single cells. *Nature Biotechnol.* 16: 737–742, 1998

Sharp, J. G., Joshi, S. S., Armitage, J. O., Bierman, P., Coccia, P. F., Harrington, D. S., Kessinger, A., Crouse, D. A., Mann, S. L., and Weisenburger, D. D.: Significance of detection of occult Non-Hodgkin's Lymphoma in histologically uninvolved bone marrow by a culture technique. *Blood* 79: 1074–1080, 1992

Sharp, J. G., Kessinger, A., Mann, S., Crouse, D. A., Armitage, J. O., Bierman, P., and Weisenburger, D. D.: Outcome of high-dose therapy and autologous transplantation in non-Hodgkin's lymphoma based on the presence of tumor in the marrow or infused hematopoietic harvest. *J.Clin.Oncol.* 14: 214–219, 1996

Shpall, E. J. and Jones, R. B.: Release of tumor cells from bone marrow. *Blood* 83: 623–625, 1994

Tricot, G., Gazitt, Y., Jagannath, S., Vesole, D., Reading, C. L., Juttner, C. A., Hoffman, R., and Barlogie, B.: CD34+ Thy+lin− peripheral blood stem cells (PBSC) effect timely trilineage engraftment in multiple myeloma (MM). *Blood* 86: 293a–0, 1995

Vannucchi, A. M., Bosi, A., Glinz, S., Pacini, P., Linari, S., Saccardi, R., Alterini, R., Rigacci, L., Guidi, S., Lombarkini, L., Longo, G., Mariani, M. P., and Rossi-Ferrini, P.: Evaluation of breast tumour cell contamination in the bone marrow and leukapheresis collections by RT-PCR for cytokeratin-19 mRNA. *Br.J.Haematol.* 103: 610–617, 1998

Vervoordeldonk, S. F., Merle, P. A., Behrendt, H., Steenbergen, E. J., van den Berg, H., van Wering, E. R., von dem Borne, A. E. G., van der Schoot, C. E., van Leeuwen, E. F., and Slaper-Cortenbach, I. C. M.: PCR-positivity in harvested bone marrow predicts relapse after transplantation with autologous purged bone marrow in children in second remission of precursor B-cell acute leukemia. *Br.J.Haematol.* 96: 395–402, 1997

Vredenburgh, J. J., Silva, O., Broadwater, G., Berry, D., DeSombre, K., Tyer, C., Petros, W. P., Peters, W. P., and Bast, J., R. C.: The significance of tumor contamination in the bone marrow from high-risk primary breast cancer patients treated with high-dose chemotherapy and hematopoietic support. *Biol. Blood Marrow Transplant.* 3: 91–97, 1997

Wagner, J. E., Collins, D., Fuller, S., Schain, L. R., Berson, A. E., Almici, C., Hall, M. A., Chen, K. E., Okarma, T. B., and Lebkowski, J. S.: Isolation of small, primitive human hematopoitic stem cells: Distribution of cell surface cytokine receptors and growth in SCID-Hu mice. *Blood* 86: 512–523, 1995

We claim:

1. An apparatus for selectively inducing a response in one or more targeted cells within a biological specimen, comprising:

a lens that defines a field of view that comprises a plurality of frames of cells within said biological specimen;

an illumination source for illuminating a frame of cells within said field of view;

an image capture system that captures an image of said frame of cells;

first commands for determining the locations of said one or more targeted cells within said image;

an energy source that emits an energy beam sufficient to induce a response in at least one of said one or more targeted cells within said frame of cells; and second commands for steering said energy beam to said locations of said one or more targeted cells.

2. The apparatus of claim 1, wherein said one or more targeted cells are identified by the presence of, or absence of, a label.

3. The apparatus of claim 2, wherein said label is directed at the cell surface.

4. The apparatus of claim 3, wherein said label comprises a monoclonal antibody.

5. The apparatus of claim 2, wherein said label comprises a membrane permeable reagent.

6. The apparatus of claim 1, wherein said illumination source comprises a diffused laser light.

7. The apparatus of claim 1, wherein said illumination source comprises an arc lamp.

8. The apparatus of claim 1, wherein said illumination source comprises a light-emitting diode.

9. The apparatus of claim 1, wherein said illumination source comprises an incandescent lamp.

10. The apparatus of claim 1, wherein said illumination source comprises a fluorescent lamp.

11. The apparatus of claim 1, wherein said illumination source only illuminates a sub-population of cells in said biological specimen.

12. The apparatus of claim 1, wherein said one or more targeted cells comprises tumor cells.

13. The apparatus of claim 1, wherein said one or more targeted cells comprises fibroblasts.

14. The apparatus of claim 1, wherein said one or more targeted cells comprises T-cells.

15. The apparatus of claim 1, wherein said one or more targeted cells comprises teratoma-forming cells.

16. The apparatus of claim 1, wherein said one or more targeted cells comprises non-tumor cells.

17. The apparatus of claim 1, wherein said image capture system comprises a camera.

18. The apparatus of claim 17, wherein said camera comprises a charge-coupled device.

19. The apparatus of claim 1, wherein said energy source comprises a laser.

20. The method of claim 19, wherein the wavelength of energy emitted from said laser is approximately between 100 nanometers and 30 micrometers.

21. The method of claim 19, wherein the wavelength of energy emitted from said laser is about 349 nanometers.

22. The method of claim 19, wherein the wavelength of energy emitted from said laser is about 355 nanometers.

23. The method of claim 19, wherein the wavelength of energy emitted from said laser is about 523 nanometers.

24. The method of claim 19, wherein the wavelength of energy emitted from said laser is about 532 nanometers.

25. The method of claim 19, wherein the wavelength of energy emitted from said laser is about 1046.

26. The method of claim 19, wherein the wavelength of energy emitted from said laser is about 1064 nanometers.

27. The apparatus of claim 1, wherein said first commands comprise commands for determining the two-dimensional locations of said one or more targeted cells within said biological specimen.

28. The apparatus of claim 1, wherein said first commands comprise commands for determining the three-dimensional locations of said one or more targeted cells within said biological specimen.

29. The apparatus of claim 1, further comprising one or more energy beam steering devices that are controlled by said second commands.

30. The apparatus of claim 29, wherein said energy beam steering devices comprise one or more elements that reflect the energy beam.

31. The apparatus of claim 29, wherein said energy beam steering devices comprise one or more elements that refract the energy beam.

32. The apparatus of claim 29, wherein said energy beam steering devices comprise one or more elements that diffract the energy beam.

33. The apparatus of claim 1, wherein said first commands are executed under the control of a computer.

34. The apparatus of claim 1, wherein said second commands are executed under the control of a computer.

35. The apparatus of claim 1, wherein said apparatus processes at least 1 square centimeter of biological specimen area per minute.

36. The apparatus of claim 1, wherein said apparatus images at least 0.25 million cells of said biological specimen per minute.

37. The apparatus of claim 1, wherein said apparatus can induce a response in at least 50 targeted cells per second.

38. The apparatus of claim 1, wherein said response induced in said one or more targeted cells is cell death.

39. The apparatus of claim 1, wherein said response induced in said one or more targeted cells comprises activation of a photosensitive agent.

40. The apparatus of claim 1, wherein said response induced in said one or more targeted cells comprises optoporation to allow entry of a substance.

41. The apparatus of claim 40, wherein said substance is genetic material.

42. The apparatus of claim 1, wherein said response induced in said one or more targeted cells comprises inactivation of a cell component.

43. The apparatus of claim 1, wherein said response induced in said one or more targeted cells comprises controlled movement of said one or more targeted cells.

44. The apparatus of claim 1, wherein said response is excitation of fluorescent dye within said one or more targeted cells.

45. The apparatus of claim 1, further comprising an energy absorbing dye in contact with said one or more targeted cells.

46. The apparatus of claim 1, further comprising third commands that control an autofocus mechanism linked to said image capture system.

47. The apparatus of claim 46, wherein said third commands are executed under the control of a computer.

48. The apparatus of claim 1, wherein said apparatus processes at least 7 square centimeters of biological specimen area per minute.

49. The apparatus of claim 1, wherein said apparatus images at least 4 million cells of said biological specimen per minute.

50. The apparatus of claim 1, wherein said apparatus can induce a response in at least 400 targeted cells per second.

51. The apparatus of claim 1, wherein said apparatus processes at least 4 square centimeters of biological specimen area per minute.

52. The apparatus of claim 1, wherein said apparatus images at least 2 million cells of said biological specimen per minute.

53. An apparatus for selectively inducing a response in one or more targeted cells within a biological specimen, comprising:

a scanning lens which focuses on a field-of-view within said biological specimen, said field-of-view comprising a plurality of frames of cells;

an illumination source that illuminates one or more frames of cells;

an image capture system that captures an image of a first frame of cells in said field-of-view;

first commands for determining the locations of said one or more targeted cells in said first frame of cells;

an energy source that emits an energy beam sufficient to induce a response in at least one of said one or more targeted cells; and second commands for steering said energy beam to said locations of said one or more targeted cells within said first frame of cells.

54. The apparatus of claim 53, further comprising:

means for directing the output of said illumination source to a second frame of cells in said field-of-view;

means for capturing an image of said second frame of cells;

third commands for determining the locations of said one or more targeted cells in said second frame of cells; and fourth commands for steering said energy beam to said locations of said one or more targeted cells within said second frame of cells.

55. The apparatus of claim 53, further comprising means for moving the position of said biological specimen with respect to said scanning lens.

56. The apparatus of claim 53, wherein said scanning lens is of F-theta design with a diameter of at least 8 mm.

57. The apparatus of claim 53, wherein said scanning lens is of F-theta design with a diameter of at least 18 mm.

58. The apparatus of claim 53, wherein said scanning lens is of F-theta design with a diameter of at least 10 mm.

59. The apparatus of claim 53, wherein said scanning lens is of F-theta design with a diameter of at least 12 mm.

60. The apparatus of claim 53, wherein said scanning lens is of F-theta design with a diameter of at least 14 mm.

61. The apparatus of claim 53, wherein said scanning lens is of F-theta design with a diameter of at least 16 mm.

62. An apparatus for identifying a first population of cells having a label within a mixture comprising said first population and a second population of cells lacking said label, comprising:

a lens that defines a field of view that comprises a plurality of frames of cells within said mixture;

an illumination source for illuminating a frame of cells in said field of view;

an image capture system that captures an image of said frame of cells; and first commands for determining the locations of at least one cell in said first population of cells having said label by reference to said image.

63. The apparatus of claim 62, further comprising a memory for storing said locations of said at least one cell in said first population of cells having said label.

64. The apparatus of claim 62, further comprising a memory for storing the quantity of cells in said first population of cells having said label.

65. The apparatus of claim 62, further comprising an energy source that emits an energy beam sufficient to induce a response in at least one cell in said first population of cells having said label.

66. An apparatus for determining a morphological or physiological characteristic of individual cells in a biological specimen, comprising:

a lens that defines a field of view that comprises a plurality of frames of cells within said biological specimen;

an illumination source for illuminating a frame of cells within said field of view;

an image capture system that captures an image of said frame of cells;

first commands for determining the location of a first targeted cell in said biological specimen by reference to said image;

second commands for intercepting said first targeted cell with an energy beam sufficient to interrogate said first targeted cell for the presence of a morphological or physiological characteristic; and a detector for measuring the response of said first targeted cell to said interrogation.

67. The apparatus of claim 66, wherein said first targeted cell is labeled with a fluorescently-tagged antibody.

68. The apparatus of claim 66, wherein said first targeted cell is labeled with two labels, wherein the first label is activated by said illumination source and the second label is activated by said energy beam.

69. The apparatus of claim 66, wherein said morphological or physiological characteristic is calcium flux.

70. The apparatus of claim 66, wherein said morphological or physiological characteristic is cell cycle status.

71. The apparatus of claim 66, wherein said morphological or physiological characteristic is cell mitotic history.

72. The apparatus of claim 66, wherein said morphological or physiological characteristic is viability.

73. The apparatus of claim 66, wherein said morphological or physiological characteristic is membrane integrity.

74. The apparatus of claim 66, wherein said morphological or physiological characteristic is intracellular pH.

75. The apparatus of claim 66, wherein said morphological or physiological characteristic is transmembrane potential.

76. The apparatus of claim 66, wherein said morphological or physiological characteristic is glutathione reductive stage.

77. The apparatus of claim 66, wherein said morphological or physiological characteristic is thiol activity.

78. The apparatus of claim 66, wherein said morphological or physiological characteristic is expression of a gene.

79. An apparatus for selectively inducing a response in one or more targeted cells within a biological specimen, comprising:

an illumination source for illuminating a frame of cells in said biological specimen;

an image capture system that captures an image of said frame of cells;

first commands for determining the locations of said one or more targeted cells within said image;

an energy source that emits an energy beam sufficient to induce a response in at least one of said one or more targeted cells within said frame of cells; and a sensor that detects the amount of energy emitted by said energy source.

80. A method for selectively inducing a response in one or more targeted cells within a biological specimen, comprising:

defining a field of view of view that comprises a plurality of frames of cells in said biological specimen;

illuminating a frame of cells within said field of view;

capturing an image of said frame of cells;

determining the locations of said one or more targeted cells within said image; and steering an energy beam to the locations of said one or more targeted cells, wherein said energy beam is sufficient to induce a response in at least one of said one or more targeted cells.

81. The method of claim 80, wherein determining the locations of said one or more targeted cells comprises determining the presence of, or absence of, a label attached to said one or more targeted cells.

82. The method of claim 80, wherein capturing an image of said frame of cells comprises capturing an image of labeled cells.

83. The method of claim 80, wherein illuminating said frame of cells comprises illuminating said frame of cells with an excitation laser light source.

84. The method of claim 80, wherein said response is selected from the group consisting of cell death, optoporation, activation of a photosensitive agent, inactivation of a cell component, controlled movement, and excitation of a fluorescent reagent.

85. A method for rapidly inducing a response in cells within a cell population, said cell population being held in a container, comprising:

defining a first field of cells that comprises a plurality of frames of cells in said biological specimen;

illuminating said first field of cells in said cell population;

capturing an image of a first fame of cells within said first field of cells;

determining the locations of first targeted cells within said first frame of cells by reference to said image; and steering an energy beam to the locations of said first targeted cells, wherein said energy beam is sufficient to induce a response in at least one of said first targeted cells.

86. The method of claim 85, further comprising:

capturing an image of a second frame of cells within said first field of cells;

determining the locations of second targeted cells within said second frame of cells by reference to said image; and steering an energy beam to the locations of said second targeted cells within said second frame of cells, wherein said energy beam is sufficient to induce a response in at least one of said second targeted cells.

87. The method of claim 86, further comprising:

illuminating a second field of cells in said cell population;

capturing an image of a first frame of cells within said second field of cells;

determining the locations of first targeted cells within said first frame of cells by reference to said image; and steering an energy beam to the locations of said first targeted cells, wherein said energy beam is sufficient to induce a response in at least one of said first targeted cells.

88. The method of claim 87, wherein illuminating said second field of cells comprises moving said container.

89. A method for selectively inducing a response in one or more targeted cells within a biological specimen, comprising:

focusing a scanning lens on a field-of-view within said biological specimen, said field-of-view comprising a plurality of frames of cells;

illuminating one or more frames of cells within said field-of-view;

capturing an image of a first frame of cells in said field-of-view;

determining the locations of said one or more targeted cells in said first frame of cells;

emitting an energy beam sufficient to induce a response in at least one of said one or more targeted cells; and steering said energy beam to the locations of said one or more targeted cells within said first frame of cells.

90. The method of claim 89, wherein said response is selected from the group consisting of cell death, optoporation, activation of a photosensitive agent, inactivation of a cell component, controlled movement, and excitation of a fluorescent reagent.

91. The method of claim 89, wherein capturing an image of said first frame of cells comprises capturing an image of labeled cells.

92. The method of claim 89, wherein said illuminating one or more frames of cells comprises illuminating said one or more frames of cells with an excitation laser light source.

93. A method for inducing a response in one or more targeted cells within a cell population, comprising:

illuminating cells in said cell population;

capturing an image of the illuminated cells;

determining the locations of said one or more targeted cells within said image;

emitting an energy beam sufficient to induce a response in at least one of said one or more targeted cells; and measuring the amount of energy contained in said energy beam; and steering said energy beam to the locations of said one or more targeted cells.

94. The method of claim 93, comprising measuring the amount of energy contained in said energy beam prior to steering said energy beam.

* * * * *

UNITED STATES PATENT AND TRADEMARK OFFICE
CERTIFICATE OF CORRECTION

PATENT NO. : 6,534,308 B1
DATED : March 18, 2003
INVENTOR(S) : Palsson et al.

It is certified that error appears in the above-identified patent and that said Letters Patent is hereby corrected as shown below:

Column 23,
Line 57, please add -- nanometers -- after the number "1046".

Signed and Sealed this

Seventh Day of September, 2004

JON W. DUDAS
*Director of the United States Patent and Trademark Office*